United States Patent
Takase et al.

(10) Patent No.: US 10,444,159 B2
(45) Date of Patent: Oct. 15, 2019

(54) OPTICAL MEASUREMENT SYSTEM

(71) Applicant: Toshiba Medical Systems Corporation, Otawara-shi (JP)

(72) Inventors: Tomohiro Takase, Otawara (JP); Isao Nawata, Otawara (JP); Motoji Haragashira, Utsunomiya (JP); Shoichi Kanayama, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/730,445

(22) Filed: Jun. 4, 2015

(65) Prior Publication Data
US 2015/0355089 A1    Dec. 10, 2015

(30) Foreign Application Priority Data

Jun. 6, 2014   (JP) .................. 2014-118215

(51) Int. Cl.
| | |
|---|---|
| *G01N 29/22* | (2006.01) |
| *G01N 21/51* | (2006.01) |
| *B01L 3/00* | (2006.01) |
| *G01N 21/77* | (2006.01) |
| *G10K 11/00* | (2006.01) |

(52) U.S. Cl.
CPC ....... *G01N 21/7703* (2013.01); *G01N 29/223* (2013.01); *G01N 29/225* (2013.01); *G10K 11/004* (2013.01); *B01L 3/5027* (2013.01)

(58) Field of Classification Search
None
See application file for complete search history.

(56) References Cited

U.S. PATENT DOCUMENTS

2003/0091284 A1*   5/2003   Maisenholder ...... G01N 21/552
                                                                        385/37
2007/0219436 A1      9/2007   Takase et al.

FOREIGN PATENT DOCUMENTS

| JP | 2007-178325 A | 7/2007 |
|---|---|---|
| JP | 2007-244736 | 9/2007 |
| JP | 2013-195404 A | 9/2013 |
| WO | WO 2013/033466 A1 | 3/2013 |

OTHER PUBLICATIONS

Japanese Office Action dated Jan. 30, 2018 in Japanese Patent Application No. 2014-118215, 5 pages.

* cited by examiner

*Primary Examiner* — Neil N Turk
(74) *Attorney, Agent, or Firm* — Oblon, McClelland, Maier & Neustadt, L.L.P.

(57) ABSTRACT

A according to one embodiment, an optical measurement system has an optical waveguide sensor chip mounted thereon, the optical waveguide sensor chip has a space defined by a plurality of surfaces including a first surface along which an optical waveguide part is provided. The optical measurement system includes a holding surface, a light transceiver, and a contact sensor. The holding surface holds the bottom surface of the optical waveguide sensor chip. The light transceiver lets light be incident on the optical waveguide sensor chip through a first window in the holding surface, and receives light that has passed through the first surface via the optical waveguide part from a second window in the holding surface. The contact sensor detects contact state in two or more detection positions located along an array direction of the first window and the second window.

10 Claims, 26 Drawing Sheets

OPTICAL MEASUREMENT SYSTEM

CROSS-REFERENCE TO RELATED APPLICATION

This application is based upon and claims the benefit of priority from Japanese Patent Application No. 2014-118215, filed Jun. 6, 2014; the entire contents of which are incorporated herein by reference.

FIELD

Embodiments described herein relate generally to an optical measurement system.

BACKGROUND

There is an optical measurement system that makes the light from the light source enter in the optical sensor and receives output light based on the incident light therefrom, thereby acquiring information on a subject from the result. Such an optical measurement system includes, for example, an optical sensor chip and a measurement unit.

The optical sensor chip is capable of retaining a sample liquid and is configured to allow light to enter therein from and exit therefrom to the outside. Having entered inside the optical sensor chip, the light is affected by a component contained in the sample liquid retained therein and is output to the outside of the optical sensor chip. The measurement unit includes at least a light transceiver and a processor. The light transceiver generates light to be incident on the optical sensor chip and receives output light therefrom. The processor processes the received output light to acquire information on the component of the sample liquid.

As one example of the optical measurement system may be cited an optical waveguide measurement system. The optical waveguide measurement system includes an optical waveguide sensor chip (hereinafter sometimes simply referred to as "sensor chip"), as an optical sensor chip. The optical waveguide measurement system is capable of measuring, for example, the density of a test object contained in a sample liquid by using waveguiding effect.

The optical waveguide sensor chip includes an optical waveguide part and a functional layer formed in the boundary between the optical waveguide part and a sample liquid container. The light incident on the optical waveguide part is affected depending on the reaction of the functional layer to a component contained in the sample liquid. The affected light is received as output light.

The optical measurement system has an attachment part. In the optical waveguide measurement system, if the measurement unit performs a measurement while not equipped properly with an optical waveguide sensor chip, for example, the light transceiver receives abnormal light. Accordingly, the measurement results in an error. In a state where the measurement unit is not equipped properly with an optical waveguide sensor chip, for example, the optical waveguide sensor chip is mounted on the placement surface of the measurement unit with the bottom surface at a predetermined angle thereto. When a measurement is performed in this state, the angle of light incident on the optical waveguide part changes by degrees of the predetermined angle. If this happens, the light may not properly propagate in the optical waveguide part. Consequently, the light transceiver receives abnormal light, and the measurement results in an error. Examples of the abnormal light include scattered light, stray light, and the like.

That is, to properly mount the optical waveguide sensor chip on the measurement unit, at least the bottom surface of the optical waveguide sensor chip needs to be in parallel to the placement surface. For this reason, the operator is required to visually check whether the bottom surface is in parallel to the placement surface each time he/she mounts the optical waveguide sensor chip on the measurement unit. However, if a number of tests, such as tests for infection, are required, this work imposes a heavy burden on the operator. In addition, the check work prolongs the time necessary for the tests.

DETAILED DESCRIPTION

In general, according to one embodiment, an optical measurement system is configured to perform optical measurement of a subject and to have an optical waveguide sensor chip mounted thereon, the optical waveguide sensor chip has a space for accommodating the subject, defined by a plurality of surfaces including a first surface on which a functional layer is formed and along which an optical waveguide part is provided. The optical measurement system includes a holding surface, a light transceiver, processing circuitry, and a contact sensor. The holding surface holds the bottom surface of the optical waveguide sensor chip. The light transceiver lets light be incident on the optical waveguide sensor chip through a first window in the holding surface, and receives light that has passed through the first surface via the optical waveguide part from a second window in the holding surface. The processing circuitry processes what is received by the light transceiver to acquire information on the subject. The contact sensor detects contact state in two or more detection positions located along an array direction of the first window and the second window.

Figure 1:
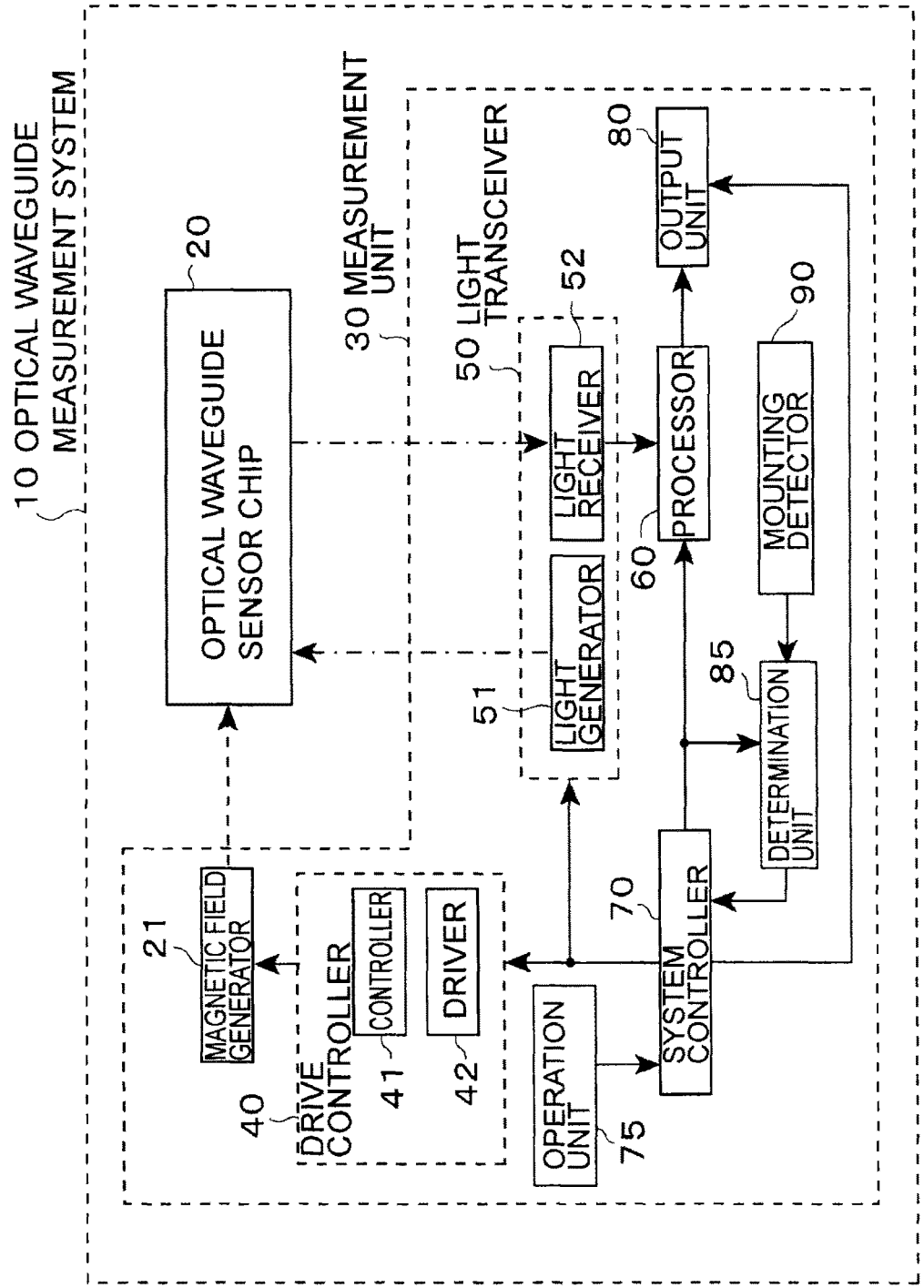
FIG. 1 is a block diagram of an example of the entire configuration of an optical waveguide measurement system according to an embodiment.
Figure 2:
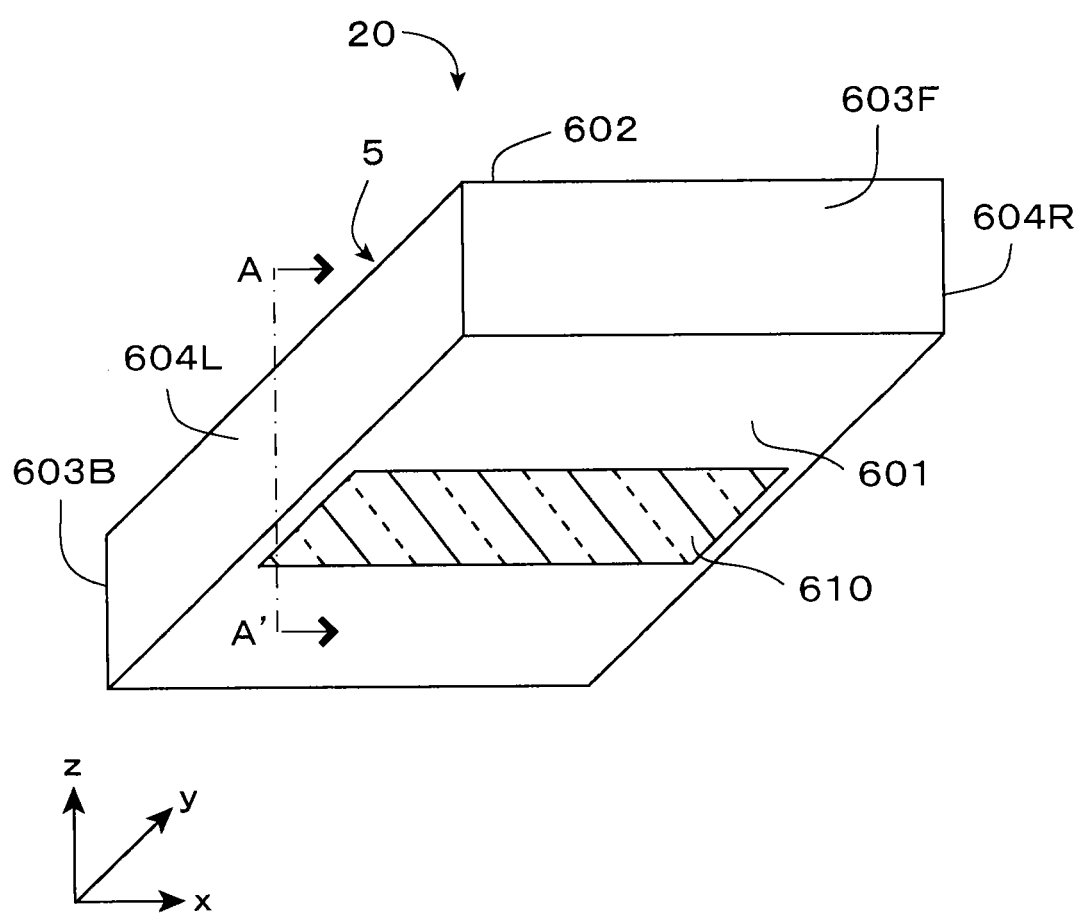
FIG. 2 is a perspective view of an example of an optical waveguide sensor chip.
Figure 3:
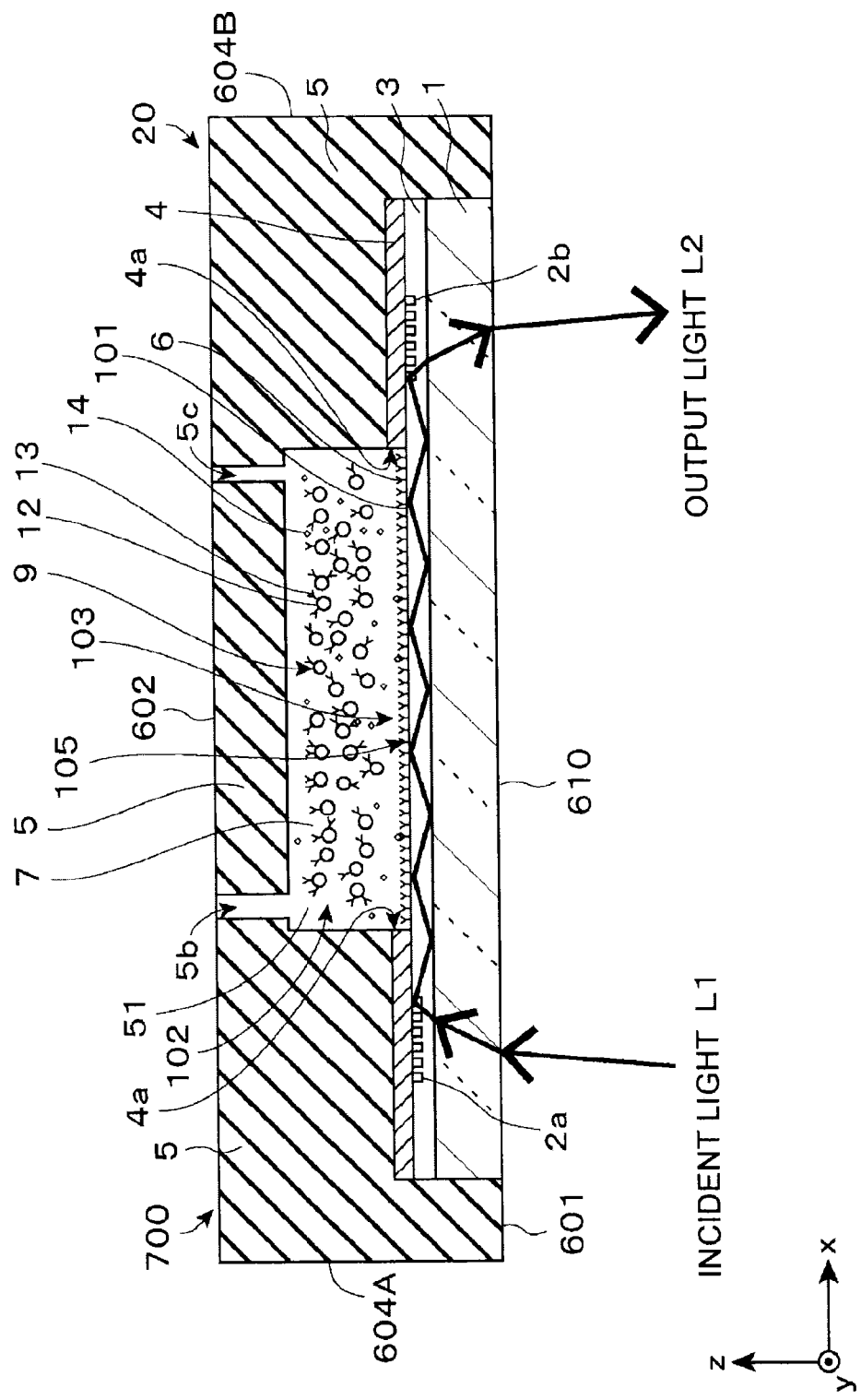
FIG. 3 is a cross-sectional view of an example of the optical waveguide sensor chip.

With reference to FIGS. 1 to 3, a description is given of the configuration of an optical waveguide measurement system 10 according to an embodiment. FIG. 1 is a block diagram of an example of the entire configuration of the optical waveguide measurement system 10 of the embodiment.

[Optical Waveguide Measurement System]

As illustrated in FIG. 1, the optical waveguide measurement system 10 includes an optical waveguide sensor chip 20 and a measurement unit 30. In the optical waveguide measurement system 10, light enters the optical waveguide sensor chip 20 from the measurement unit 30. The measurement unit 30 receives light output from the optical waveguide sensor chip 20 and processes it, thereby acquiring information on a subject. The optical waveguide sensor chip 20 is formed as a separate body from the measurement unit 30. In this embodiment, the configuration of the optical waveguide sensor chip 20, that of the measurement unit 30, and that of a combination of them are described in this order.

(Optical Waveguide Sensor Chip)

Regarding the optical waveguide sensor chip 20, the outer structure is described referring to FIG. 2, and the inner structure is described referring to FIG. 3. FIG. 2 is a perspective view of an example of the optical waveguide sensor chip 20. FIG. 3 is a cross-sectional view taken along line A-A' in FIG. 2. In the drawings, the x direction is a direction parallel to the lateral direction of the optical waveguide sensor chip 20, the y direction is a direction parallel to the longitudinal direction of the optical waveguide sensor chip 20, and the z direction is a direction perpendicular to the x and y directions. For convenience of explanation, the z direction is sometimes referred to as "upward direction", "vertical direction", and "vertically upward direction". Besides, the y direction is sometimes referred to as "first direction", while the x direction is sometimes referred to as "second direction". Note that a description of "upward direction" and the like in the following does not limit the use conditions of the optical waveguide sensor chip 20.

FIG. 2 illustrates the optical waveguide sensor chip 20 viewed from an obliquely downward direction in the directions defined as above. The line A-A' in FIG. 2 corresponds the center of a window 610 in the lateral direction.

As illustrated in FIG. 3, the optical waveguide sensor chip 20 includes an outer casing 5, a transparent substrate 1, an optical waveguide part 3, and a protective part 4. Part of the lower surface (bottom surface 601) of the outer casing 5 forms an opening, in which the transparent substrate 1, the optical waveguide part 3, and the protective part 4 are arranged. The transparent substrate 1 is located at the bottom, and the optical waveguide part 3 is arranged thereon. The protective part 4 is placed on the optical waveguide part 3, and part of the protective part 4 forms an opening (opening 4a). The outer casing 5, the optical waveguide part 3, the protective part 4, and the like define a reaction space 102. The optical waveguide sensor chip 20 is configured to be capable of retaining a sample liquid that contains a test object (test article) in the inside, i.e., in the reaction space 102. In the following, the configuration of each unit is described. Incidentally, the optical waveguide sensor chip 20 is sometimes identified with the outer casing 5.

<Outer Casing>

As illustrated in FIG. 2, the outer casing 5 is formed substantially in a rectangular parallelepiped shape. The outer casing 5 has the bottom surface 601 as the lower surface and an upper surface 602. In addition, the outer casing 5 has a front surface 603F and a back surface 603B that extend along its lateral direction. Further, the outer casing 5 has a right surface 604R and a left surface 604L that extend along its longitudinal direction. As illustrating the optical waveguide sensor chip 20 viewed from the back, FIG. 2 has reversed right and left from those of the optical waveguide sensor chip 20. The bottom surface 601 of the outer casing 5 is provided with the window 610 that allows light to enter the inside of the optical waveguide sensor chip 20. As described above, light enters the optical waveguide sensor chip 20 from the measurement unit 30 through the window 610 of the outer casing 5. Having entered through the window 610, the light is affected depending on the density of a test article retained in the reaction space 102. The affected light is output through the window 610, and received by the measurement unit 30.

<<Window>>

The window 610 is formed in a rectangular shape. The longitudinal direction of the window 610 is in parallel to the longitudinal direction of the outer casing 5. Similarly, the lateral direction of the window 610 is in parallel to the lateral direction of the outer casing 5. The window 610 is located in a position, for example, where the long central axis of the window 610 and the short central axis of the optical waveguide sensor chip 20 lie in the same straight line. The window 610 may be located in any position in the longitudinal direction of the bottom surface 601. One of the front surface 603F and the back surface 603B may be an inclined surface so that they are distinguishable. For example, if the bottom surface 601 is shorter than the upper surface 602 in the longitudinal direction of the outer casing 5, an edge of the upper surface 602 projects more than a corresponding edge of the bottom surface 601 in the longitudinal direction.

In this case, the front surface 603F is formed as an inclined surface. Further, the front surface 603F may be formed such that a portion extending upward from the bottom surface 601 is a vertical surface, while the rest is an inclined surface. With this, the optical waveguide sensor chip 20 has the upper surface 602 smaller in area than the bottom surface 601. Incidentally, in this embodiment, the window 610 is formed of the opening in the bottom surface of the outer casing 5 and the transparent substrate 1. However, in the following, the window 610 may only refer to the opening of the outer casing 5 or the transparent substrate 1.

In the lateral direction of the outer casing 5, in a space above the window 610, at least a region on the upper surface 602 side is formed shorter than the window 610. The region corresponds to the reaction space 102, and is described in detail later as the reaction space 102.

The outer casing 5 can be made of a material resistant to a sample liquid, a reagent, or the like. For example, the outer casing 5 is made of resin or the like. The outer casing 5 is formed to block light that directly enters the reaction space 102 and the optical waveguide part 3 from the outside. The outer casing 5 is formed of, for example, dark colored material such as black material. If the outer casing 5 is made of a black material, the entire optical waveguide sensor chip 20 appears black. Hereinafter, the optical waveguide part 3, the protective part 4, and the outer casing 5 that form the reaction space 102 are sometimes collectively referred to as "reaction container 700".

<<Holes>>

As illustrated in FIG. 3, the upper surface 602 of the outer casing 5 is provided with a hole 5b for introducing a sample liquid, a reagent, or the like into the reaction space 102 and a hole 5c for releasing pressure from the reaction space 102. Incidentally, there may be a plurality of each of the holes 5b and 5c.

<Transparent Substrate>

The transparent substrate 1 is formed in a plate-like shape. The transparent substrate 1 is arranged in such a manner that, for example, the bottom surface is located in the same plane as a bottom surface 5a of the outer casing 5. In other words, the bottom surface of the transparent substrate 1 forms the window 610. The optical waveguide sensor chip 20 is configured such that light from the measurement unit 30 enters the optical waveguide part 3 through the transparent substrate 1, and also light is output to the measurement unit 30 through the transparent substrate 1. This light includes at least visible light. Accordingly, for example, the transparent substrate 1 may be made of a variety of material having a high transmittance of visible light. The transparent substrate 1 may also be made of material with high barrier properties of moisture and gas that come in the reaction space 102 from the outside as well as having excellent resistance to solvents and weather. Examples of the material include transparent inorganic materials such as quartz, glass, and the like, and transparent plastic materials such as polyethylene terephthalate, polycarbonate, phenol resins, epoxy resins, acrylic resins, polyimide, polyamide, and the like.

<Optical Waveguide Part>

The optical waveguide part 3 is laminated on the upper surface of the transparent substrate 1. The optical waveguide part 3 propagates light that has entered from the measurement unit 30 through the transparent substrate 1 and light affected depending on the density of a test article retained in the reaction space 102.

As described below, at least part of the upper surface of the optical waveguide part 3 forms the bottom surface among a plurality of surfaces of the reaction space 102. For example, the optical waveguide part 3 is formed as a core of a slab optical waveguide having the same shape as the window 610. That is, the optical waveguide part 3 is held between the transparent substrate 1 and the protective part 4 using them as cladding, thereby forming a core/cladding structure. Alternatively, the optical waveguide part 3 is held between the transparent substrate 1 and a solution medium 7 that fills the reaction space 102 using them as cladding, thereby forming a core/cladding structure.

The optical waveguide part 3 is made of transparent material having a higher refractivity than that of the transparent substrate 1, the protective part 4, and the solution medium 7. The material for the optical waveguide part 3 may be selected from the above transparent materials as appropriate. The thickness of the optical waveguide part 3 may be, for example, 3 μm to 300 μm. While the optical waveguide part 3 may be made of material selected as appropriate from the above transparent materials, if the transparent substrate 1 is made of, for example, glass such as alkali-free glass, the optical waveguide part 3 is made of transparent organic resin having a higher refractivity than that of the glass.

<Grating>

A grating 2a deflects the optical path of incident light L1 from the window 610 in the optical waveguide part 3 to enable optical waveguiding. In other words, the grating 2a diffracts light incident on the optical waveguide part 3 at a predetermined angle. The light incident on the grating 2a from the optical waveguide part 3 is diffracted to deflect the optical path, and thus is incident on the interface between the optical waveguide part 3 as a core and surfaces that form cladding (the transparent substrate 1 and a surface formed of the protective part 4 and the solution medium 7) at an angle less than the supplementary angle of the critical angle. Thus the incident light can be propagated through the optical waveguide part 3. Described below is the configuration of the gratings 2a and 2b.

The gratings 2a and 2b are arranged in portions in contact with the optical waveguide part 3 to be spaced apart by a predetermined distance in the longitudinal direction of the window 610 (x direction). The portions in contact with the optical waveguide part 3 in which the gratings are arranged may be, for example, inside the optical waveguide part 3, inside the transparent substrate 1 or the bottom surface of the protective part 4. The grating 2a is located near an edge of a portion in contact with the optical waveguide part 3 on a side where light is incident on the optical waveguide part 3 from the transparent substrate 1. The grating 2b is located near an edge of a portion in contact with the optical waveguide part 3 on a side where light is output from the transparent substrate 1 to the optical waveguide part 3. In the following, an example is described in which the gratings 2a and 2b are formed inside the optical waveguide part 3 in contact with the boundary between the optical waveguide part 3 and the protective part 4. However, the embodiment is not limited to this. For example, the gratings 2a and 2b may be formed inside the optical waveguide part 3 in contact with the boundary between the optical waveguide part 3 and the transparent substrate 1, or inside the transparent substrate 1 in contact with the boundary.

The grating 2b deflects the optical path of light waveguided by the optical waveguide part 3 so that the light can be output to the outside. That is, light incident on the optical waveguide part 3 through the grating 2a is totally reflected a plurality of times in the optical waveguide part 3 and then incident on the grating 2b. Having been incident on the grating 2a, the light is diffracted by the grating 2b and thereby the optical path is deflected. Thus, the light is emitted at a predetermined angle from the optical waveguide part 3 to the outside.

The gratings 2a and 2b are each formed of a plurality of gratings having a predetermined pitch dimension, which are arranged at predetermined intervals in the longitudinal direction of the window 610 (x direction). The gratings have an elongated shape extending in the lateral direction of the window 610 (y direction). The upper surface of the gratings abuts on the protective part 4 and is formed in the boundary between the optical waveguide part 3 and the protective part 4. The gratings are aligned in a direction, for example, parallel to the lateral direction of the optical waveguide sensor chip 20 (x direction). That is, in the optical waveguide part 3, light is wave-guided in the lateral direction of the optical waveguide sensor chip 20 (second direction; x direction). However, this is not so limited. For example, the gratings may be aligned in a direction parallel to the longitudinal direction of the optical waveguide sensor chip 20 (first direction; y direction).

The gratings of the grating 2a are formed so that light can be incident on the optical waveguide part 3 from therefrom. On the other hand, the gratings of the grating 2b are formed so that light from the optical waveguide part 3 can be output therefrom. The gratings are made of transparent material having a higher refractivity than that of the transparent substrate 1. The material and shape of the gratings may be determined as appropriate based on the angle of light incident on the gratings or the like. The gratings may be made of transparent material selected as appropriate from the above transparent inorganic materials, transparent plastic materials, and transparent oxide materials such as titanium oxide ($TiO_2$), tin oxide ($SnO_2$), zinc oxide, lithium niobate, gallium arsenide (GaAs), indium-tin oxide (ITO), and the like. The gratings 2a and 2b may have a convex-concave pattern formed on the upper surface of the optical waveguide part 3 by photolithography or the like, or the gratings may be formed in a convex-concave pattern.

<Protective Part>

The protective part 4 is laminated on the transparent substrate 1 to sandwich the optical waveguide part 3 between the protective part 4 and the transparent substrate 1. As laminated in the optical waveguide part 3, the protective part 4 forms a plane protective layer. As illustrated in FIG. 3, the protective part 4 has an opening to expose the main surface (e.g., upper surface) of the optical waveguide part 3. In the following, inside vertical surfaces of the protective part 4 which define the opening are referred to as opening 4a. The main surface exposed by the opening 4a corresponds to a sensing surface 101 (described later). The opening 4a of the protective part 4 has, for example, a rectangular shape. The main surface of the optical waveguide part 3 exposed by the opening 4a is the sensing surface 101 (described later). Light incident on a surface of the protective part 4 in contact with the optical waveguide part 3 is totally reflected by the surface. When the protective part 4 is made of, for example, transparent material, it may be made of material having a lower refractivity than that of the optical waveguide part 3. Examples of the material for the protective part 4 include the above transparent material, those not reactive to the solution medium 7 retained in the reaction space 102, fluorine resin, and the like.

The outer casing 5 is formed to surround the opening 4a. The reaction space 102 described next is formed as the opening 4a is surrounded by the outer casing 5.

<Reaction Space>

The reaction space 102 is a closed space having the main surface exposed through the opening of the protective part 4 as the bottom surface and is at least enclosed by the bottom surface and the outer casing 5. A functional layer 105 formed of a plurality of first antibodies 6 (described later) is arranged on the main surface. The functional layer 105 is laminated to form the sensing surface 101.

The reaction space 102 is, for example, vacant in advance. Upon measurement by the optical waveguide measurement system 10, for example, a sample liquid that contains the solution medium 7 and an antigen 14 as well as a reagent that contains the solution medium 7 and a solid dispersion elements 9 are injected in the reaction space 102 from the outside. With this, the reaction space 102 retains the antigen 14 and second antibodies 13 that constitute the solid dispersion elements 9 in addition to the first antibodies 6 that constitute the functional layer 105.

In the optical waveguide sensor chip 20, the reaction between the functional layer 105 and a test article affects light wave-guided in the optical waveguide part 3. The light is output from the optical waveguide part 3 through the transparent substrate 1 (the window 610). For example, the incident light L1 (sometimes referred to as "input light") is attenuated depending on the amount of the antigen 14 retained in the reaction space 102. An example of a configuration for the reaction between the functional layer 105 and a test article is given in the following description of a sensing area 103.

<<Sensing Area>>

The sensing area 103 is an area where near-field light (evanescent light) can be generated when light propagates through the optical waveguide part 3. Specifically, the sensing area 103 is an area from the surface of the optical waveguide part 3 to the vicinity of the surface in the reaction space 102. As described above, the optical waveguide part 3 forms the core of a core/cladding structure. In one example of the core/cladding structure, one of two claddings that sandwich the optical waveguide part 3 is the solution medium 7 that fills the reaction container 700, and the other is the transparent substrate 1. In this structure, the sensing area 103 is located near the boundary between the core and the cladding formed of the solution medium 7. As described above, the first antibodies 6 are fixed to the sensing surface 101 in the optical waveguide part 3. The first antibodies 6 are bonded to the second antibodies 13 via the antigen 14, and thereby the sensing surface 101 is bonded to the solid dispersion elements 9 via the antigen 14. Thus, the solid dispersion elements 9 are held in the vicinity of the sensing surface 101.

While light is propagating through the optical waveguide part 3, near-field light is generated on the surface of the optical waveguide part 3. In other words, near-field light is generated in a portion of the sensing surface 101 where the light propagating through the optical waveguide part 3 is totally reflected. The near-field light seeps out of the sensing surface 101 by a distance about a fraction of the wavelength of the propagating light. If the propagating light is visible, the near-field light seeps out of the surface of the optical waveguide part 3 into the reaction space 102 by a distance in a range of about 50 nm to 500 nm, for example. In this case, the sensing area 103 is an area extending vertically upward by about 50 nm to 500 nm from the surface of the optical waveguide part 3.

The reaction space 102 communicates with the outside via the hole 5c. When a test liquid is supplied to the reaction space 102, the air in the reaction space 102 is discharged from the hole 5c to the outside.

(Antibodies, Magnetic Microparticles, Etc.)

The antigen 14 and the first antibodies 6, and also the antigen 14 and the second antibodies 13 specifically bind together by an attractive force due to antibody-antigen reaction. Through the antibody-antigen reaction, the first antibodies 6 bind to the second antibodies 13 via the antigen 14. Incidentally, while the antigen 14, the first antibodies 6, and the second antibodies 13 are minute with respect to magnetic microparticles 12, they may be illustrated in the same size to schematically indicate binding reactions between the antigen 14 and the first and second antibodies 6 and 13 (in FIG. 3, etc.).

<First Antibodies>

The first antibodies 6 are substances that specifically react with the antigen 14 due to antibody-antigen reaction. The sensing surface 101 and the first antibodies 6 are fixed by, for example, hydrophobic interaction, chemical bond, or the like between the first antibodies 6 and the sensing surface 101. When the antigen 14 is a test article, the first antibodies 6 specifically bind to the test article. Those that specifically bind to the test article may sometimes be referred to as first substances or second substances. In this case, the first antibodies 6 correspond to the first substances.

<Solid Dispersion>

The solid dispersion elements 9 include carriers which carry the second antibodies 13. The second antibodies 13 that constitute the solid dispersion elements 9 bind to the first antibodies 6 via the antigen 14, and thereby the solid dispersion elements 9 are fixed in the vicinity of the sensing surface 101. At this time, if near-field light is generated on the sensing surface 101, the carriers that constitute the solid dispersion elements 9 disperse and absorb the light.

The carriers may be of any type as long as they can be dispersed in the solution medium 7; typically, solid particles are selected as the carriers. The solid particles include gel particles and sol particles. The solid particles may be microparticles with a small average primary particle diameter. The average primary particle diameter of the microparticles may be, for example, 0.05 µm to 200 µm. Further, the average primary particle diameter of the microparticles may be, for example, 0.2 µm to 20 µm. Through the use of microparticles having such average primary particle diameter, it is possible to increase the scattering efficiency of near-field light generated in the sensing area 103 in the vicinity of the sensing surface 101. In this embodiment, the magnetic microparticles 12 (described later) having magnetic properties are used as the carriers.

When the reaction space 102 is filled with the solution medium 7 and the solid dispersion elements 9 are introduced into the solution medium 7, the solid dispersion elements 9 move as being dispersible in the solution medium 7. The solution medium 7 and the solid dispersion elements 9 are selected such that the gravity on the solid dispersion elements 9 at this time is larger than the sum of the buoyancy applied thereto in the reverse direction to the gravity and the resistance from the solution medium 7. The solution medium 7 is made of a liquid.

The dispersion, absorption, and the like of the near-field light in the sensing area 103 affect light that propagates through the optical waveguide part 3. When the solid dispersion elements 9 enter the sensing area 103, the near-field light is scattered with the solid dispersion elements 9. The near-field light attenuates due to the dispersion. The attenuation of the near-field light affects light that is wave-guided through the optical waveguide part 3. That is, if the near-field light attenuates, the light that is wave-guided through the optical waveguide part 3 also attenuates accordingly. In other words, if the near-field light is dispersed and absorbed strongly in the sensing area 103, this reduces the intensity of the light that propagates through the optical waveguide part 3. This means that as the amount of the solid dispersion elements 9 increases in the sensing area 103, the intensity of light output from the optical waveguide part 3 decreases. Here, the light that is wave-guided through the optical waveguide part 3 refers to light that propagates (is wave-guided) while being repeatedly reflected in the interface to the optical waveguide part 3.

In this manner, the optical waveguide sensor chip 20 includes the sensing surface 101, and retains the solid dispersion elements 9 and the antigen 14 in the reaction space 102 in contact with the sensing surface 101. With this, near-field light generated in the sensing surface 101 attenuates, resulting in a change in the intensity of light output from a light transceiver 50.

<<Magnetic Microparticles>>

The magnetic microparticles 12 are at least partly formed of magnetic material. For example, the magnetic microparticles 12 are formed by coating the surface of particles made of magnetic material with polymer material. The magnetic microparticles 12 may also be formed by coating the surface of particles made of polymer material with magnetic material. The magnetic microparticles 12 may be particles made of magnetic material. In this case, the magnetic microparticles 12 have a measure to bind the second antibodies 13 to the surfaces of the particles by hydrophobic bonding, covalent bonding, or the like. Examples of the magnetic material for the magnetic microparticles 12 include ferrimagnetic materials and ferromagnetic materials. Examples of the ferrimagnetic materials include variety of ferrites such as γ-Fe2O3. Examples of the magnetic material used for the magnetic microparticles 12 include, in addition to the above, superparamagnetic material that swiftly loses magnetic properties when magnetic field application is stopped. With the use of superparamagnetic material for the magnetic microparticles 12, the solid dispersion elements 9 that have been magnetized and aggregated can be easily dispersed. Specifically, in the measurement unit 30 (described later), a magnetic field is sometimes applied for measurement. Upon magnetic field application, the solid dispersion elements 9 may be aggregated as being magnetized. The aggregation of the solid dispersion elements 9 presents an obstacle to the measurement, and therefore the solid dispersion elements 9 need to be dispersed. If made of superparamagnetic material, the solid dispersion elements 9 can be easily dispersed.

To further improve the dispersion at the stop of magnetic field application, the magnetic microparticles 12 may be provided with a positive or negative charge on its surface. Besides, when the solution medium 7 is a liquid, a dispersant such as a surfactant may be added to the solution medium 7. These are effective for the dispersion of the solid dispersion elements 9 when magnetic field application to the reaction space 102 is stopped. For example, this can promote the stirring of the solid dispersion elements 9 and the antigen 14 mixed in the solution medium 7. As a result, the reaction progresses between the antigen 14 and the solid dispersion elements 9, thereby achieving highly accurate measurement.

<<Second Antibodies>>

The second antibodies 13 are substances that specifically react with the antigen 14. The second antibodies 13 correspond to the second substances. The second antibodies 13 are fixed to the surfaces of the magnetic microparticles 12. The second antibodies 13 may be the same as or different from the first antibodies 6. As just mentioned, the second antibodies 13 are fixed to the surfaces of the magnetic microparticles 12. This fixation may be accounted for, for example, physisorption or chemical bond via carboxyl groups, amino groups, and the like. If, for example, a test article in a sample liquid is an antigen, the second substances may be used as antibodies (secondary antibodies); however, the combination of the antigen 14 and the first or second substances is not limited to the combination of an antigen and an antibody. For example, if the antigen 14 is sugar, the first or second substances are lectin. If the antigen 14 is a nucleotide chain, the first or second substances are nucleotide chain complementary to it. Further, if the antigen 14 is ligand, the first or second substances are an acceptor for it. The second antibodies 13 are substances that specifically react with the antigen 14 due to antibody-antigen reaction. When the antigen 14 is a test article, the second antibodies 13 correspond to the second substances that specifically bind to the test article. The first antibodies 6 and the second antibodies 13 may sometimes be correctively referred to as "antibodies".

When the functional layer 105 binds to the solid dispersion elements 9 via the antigen 14, the solid dispersion elements 9 stay in the sensing area 103. At this time, if light is being wave-guided through the optical waveguide part 3, near-field light generated in the sensing area 103 is dispersed. As a result, the intensity of the light that is wave-guided through the optical waveguide part 3 is attenuated.

Incidentally, not all the solid dispersion elements 9 that stay in the sensing area 103 are those specifically binding to the functional layer 105 via the antigen 14 to be measured. Therefore, the solid dispersion elements 9 not related to the measurement are required to be separate from the sensing area 103. For example, the solid dispersion elements 9 may be moved by an action through medium due to the magnetic field. In this case, the solid dispersion elements 9 contain the magnetic microparticles 12.

Thus, the optical waveguide measurement system 10 can measure the amount, density, and the like of the antigen 14 retained in the reaction space 102 based on the intensity of the light and the time series variation of the intensity. That is, the optical waveguide sensor chip 20 is configured such that light that propagates through the optical waveguide part 3 is attenuated according to the internal environment of the reaction space 102. The internal environment of the reaction space 102 may be indicated by a variety of parameters. Examples of the parameters for the internal environment include the density of the antigen 14 as a test article. In other words, depending on the density of the antigen 14 as a parameter for the internal environment, the degree of the attenuation of light that propagates through the optical waveguide part 3 is determined.

(Measurement Unit)

Figure 4:
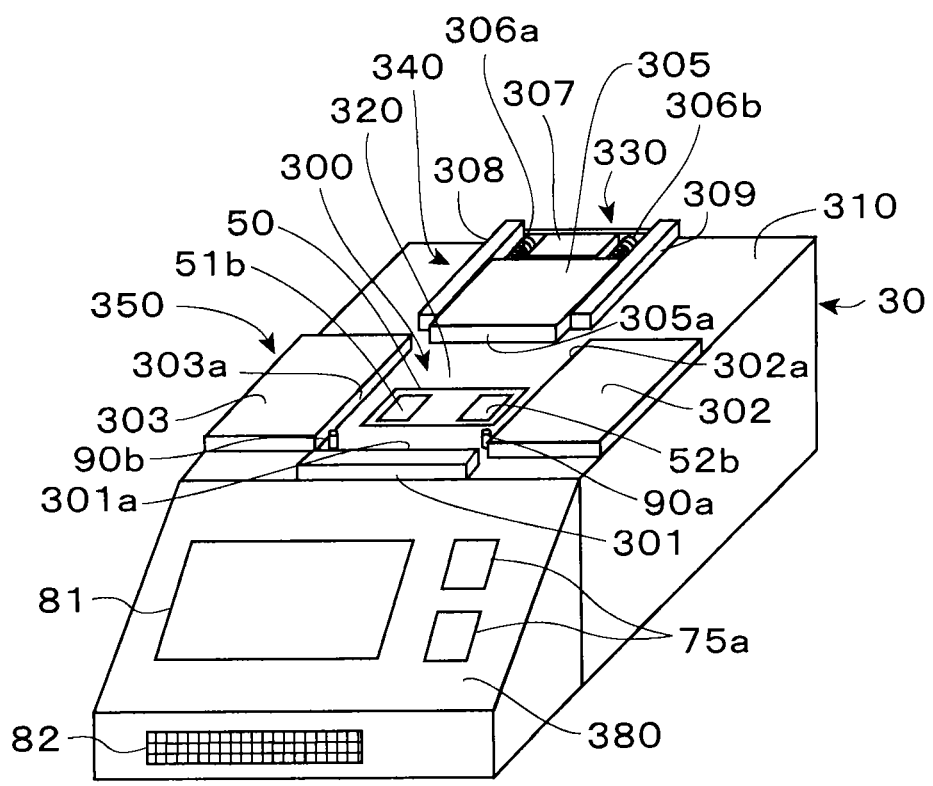
FIG. 4 is a perspective view of an example of a measurement unit.

FIG. 4 is a perspective view of an example of the measurement unit 30. In the figure, the z direction corresponds to the upward direction, the vertical direction, or the upward vertical direction. The x direction is the right direction of the measurement unit 30, while the y direction is the back direction. In addition, the y direction and a direction opposite thereto (the front-back direction) may sometimes be referred to as "first direction". Similarly, the x direction and a direction opposite thereto (the left-right direction) may sometimes be referred to as "second direction". Note that "upward direction" and the like in the following description are definitions for convenience of explanation, and are not intended to limit the use condition or the installed condition of the measurement unit 30.

As illustrated in FIG. 4, the measurement unit 30 is formed in the shape of a box having an upper surface 310 in parallel to the xy directions. The measurement unit 30 includes therein a light transceiver, a memory, a central processing unit (CPU), and the like, which implement functions of the measurement unit 30. The upper surface 310 of the measurement unit 30 is provided with an attachment part 300. The measurement unit 30 has a front surface 380 provided with a display 81, a notification unit 82, and a plurality of switches 75a as an output unit 80. The front surface 380 is inclined to facilitate the viewability. They may be located in any part other than where the attachment part 300 is arranged on the upper surface 310.

<Attachment Part>

The attachment part 300 includes a first mechanism 340, a second mechanism 350, and a holding surface 320. The first mechanism 340 is configured to be capable of holding or sandwiching the optical waveguide sensor chip 20 in the longitudinal direction thereof. The second mechanism 350 includes a pair of contact surfaces that restrains the optical waveguide sensor chip 20 in the lateral direction thereof. The holding surface 320 is a surface for holding the bottom surface of the optical waveguide sensor chip 20.

The first mechanism 340 holds the optical waveguide sensor chip 20 from the front surface 603F and the back surface 603B. The second mechanism 350 restrains the right surface 604R and the left surface 604L of the optical waveguide sensor chip 20. In this manner, the attachment part 300 holds the optical waveguide sensor chip 20 while surrounding it from the four directions. The holding surface 320 is part of the upper surface 310 enclosed by the first mechanism 340 and the second mechanism 350. With this, the optical waveguide sensor chip 20 is restrained by the attachment part 300 in at least the front-back direction, the left-right direction, and the z direction.

<First Mechanism>

The first mechanism 340 includes a movable part 305, a movable mechanism 330, and a first contact part 301. The movable mechanism 330 is configured to be capable of reciprocating the movable part 305 along the front-back direction (±y direction). The first contact part 301 is located in a position facing the movable part 305. The first mechanism 340 corresponds to an example of a mechanism. The first contact part 301 corresponds to an example of a fixed holding part. Either or both the movable part 305 and the movable mechanism 330 correspond to an example of a movable holding part.

<<Movable Part>>

The movable part 305 includes a movable surface 305a facing forward. When the optical waveguide sensor chip 20 is mounted on the attachment part 300, the movable surface 305a is in contact with the front surface 603F of the optical waveguide sensor chip 20. The movable part 305 is reciprocated by the movable mechanism 330 of the first mechanism 340 (described later) along the front-back direction.

<<Movable Mechanism>>

The movable mechanism 330 includes guides 308 and 309, elastic parts 306a and 306b, and a stopper 307. The elastic parts 306a and 306b are coupled with a surface of the movable part 305 opposite to the movable surface 305a. The elastic parts 306a and 306b are, for example, springs that expand and contract in the front-back direction. The elastic parts 306a and 306b bias the movable part 305 forward.

The stopper 307 is located, for example, between the elastic parts 306a and 306b, and confines the backward moving distance of the movable surface 305a. The guides 308 and 309 limit the movement of the movable part 305 in the left-right direction (the second direction) and the vertically upward direction. If the movable part 305 is formed in a substantially rectangular parallelepiped shape, the guides 308 and 309 each have an elongated shape extending in the front-back direction. A side surface of the guide 308 and that of the guide 309 hold the movable part 305 from both side surfaces perpendicular to the movable surface 305a. The stopper 307 includes a flange (not illustrated) that restrains the upper surface of the movable part 305. Thus, the movement of the movable part 305 is limited in the left-right direction and the vertically upward direction. Besides, the stopper limits the backward movement of the movable part 305 to a predetermined distance.

<<First Contact Part>>

The first contact part 301 is located on the upper surface 310 in a position facing the movable part 305. The first contact part 301 includes a front contact surface 301a that faces the movable surface 305a at a predetermined distance. The predetermined distance is determined according to the longitudinal length of the outer casing 5 of the optical waveguide sensor chip 20 and the moving distance of the movable surface 305a by the elastic parts 306a and 306b. That is, the front contact surface 301a faces backward, and is in contact with the back surface 603B of the optical waveguide sensor chip 20 mounted on the attachment part 300. Here, the distance between the movable surface 305a and the front contact surface 301a is shorter than the longitudinal length of the optical waveguide sensor chip 20. When no force is applied to the movable surface 305a from the outside in resistance to the biasing force, the difference between the length of the optical waveguide sensor chip 20 and the distance between the movable surface 305a and the front contact surface 301a is shorter than the distance that the movable part 305 can move backward. With this, a backward force is applied to the front surface 603F from the movable surface 305a while the optical waveguide sensor chip 20 is being mounted. Thus, the first mechanism 340 holds the optical waveguide sensor chip 20 from the front surface 603F and the back surface 603B extending along the lateral direction thereof, and limits the backward movement of the optical waveguide sensor chip 20.

When the optical waveguide sensor chip 20 is mounted on the attachment part 300, the first mechanism 340 limits the movement of the optical waveguide sensor chip 20 in the vertically upward direction. The limit of the movement is achieved by the friction between the movable surface 305a and the front surface 603F as well as the friction between the front contact surface 301a and the back surface 603B. For example, the first mechanism 340 may be provided with an engagement part to limit the movement. In this case, the optical waveguide sensor chip 20 is also provided with an engagement part configured to be engaged with the engagement part of the first mechanism 340. If the optical waveguide sensor chip 20 is provided with an engagement part, the engagement part corresponds to an example of a movement limiter. The engagement part is, for example, an engagement claw that is in contact with the upper surface 602 of the optical waveguide sensor chip 20 while the optical waveguide sensor chip 20 is being mounted, thereby limiting the movement of the optical waveguide sensor chip 20 in the vertically upward direction. The engagement claw corresponds to an example of a movement limiter that applies a vertically downward force to the optical waveguide sensor chip 20. For example, the engagement claw extends backward from the front contact surface 301a.

Figure 5:
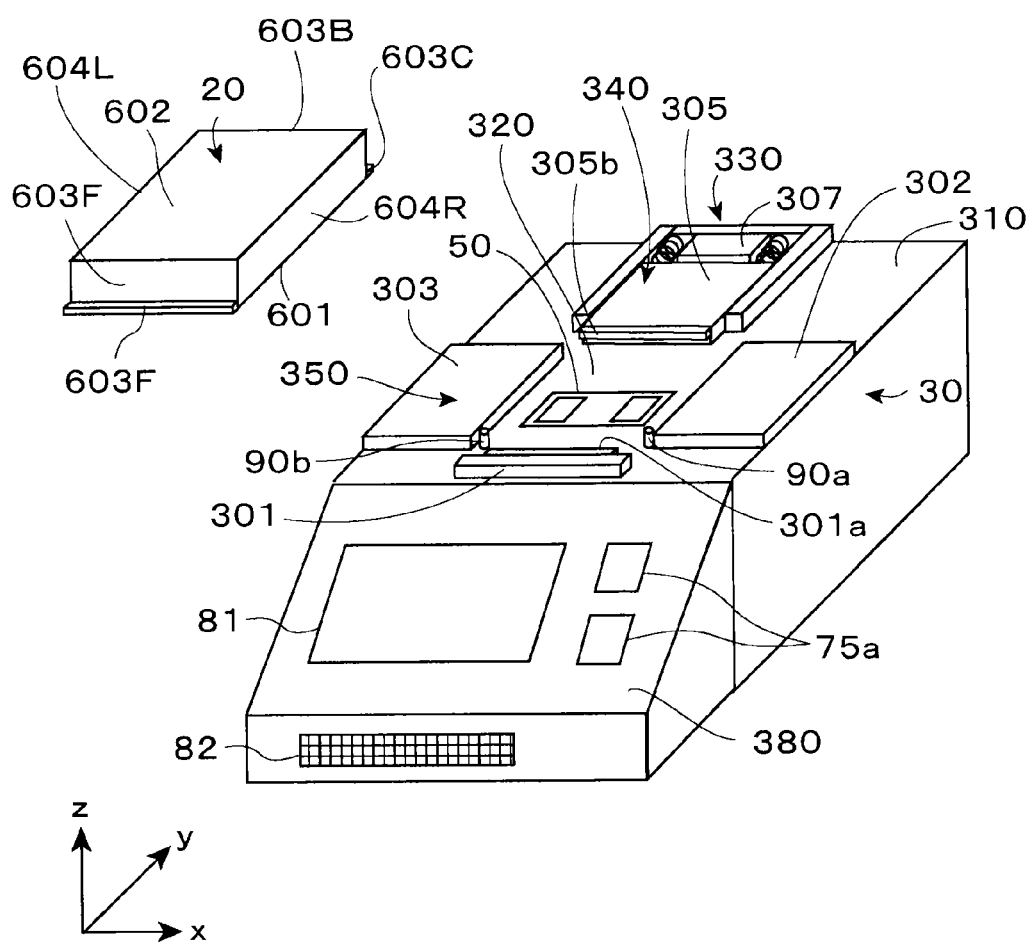
FIG. 5 is a perspective view of an example of an attachment part provided with an engagement part.

FIG. 5 is a perspective view of an example of the attachment part 300 provided with an engagement part. In the example of FIG. 5, the back surface 603B and the front surface 603F of the optical waveguide sensor chip 20 are provided with flanges 603C and 603D, respectively. In this case, the first mechanism 340 has an engagement part that engages with the flanges 603C and 603D. The flange 603C is a protrusion that protrudes from the front surface 603F in the longitudinal direction of the optical waveguide sensor chip 20. The bottom surface of the protrusion as the flange 603C is located in the same plane as the bottom surface 601 of the optical waveguide sensor chip 20. Similarly, the flange 603D is a protrusion that protrudes from the back surface 603B in the longitudinal direction of the optical waveguide sensor chip 20. The bottom surface of the protrusion as the flange 603D is located in the same plane as the bottom surface 601 of the optical waveguide sensor chip 20.

The engagement part of the first mechanism 340 is arranged on at least one of the movable surface 305a and the front contact surface 301a. On the movable surface 305a, the engagement part is arranged near the vertical center thereof. The engagement part is referred to as a protrusion 305b. The flange 603C of the optical waveguide sensor chip 20 is fitted in a recess formed by the protrusion 305b, the movable surface 305a, and the holding surface 320. In the example of FIG. 5, the movable surface 305a having the protrusion 305b engages with the front surface 603F provided with the flange 603C in an L-shape. Thereby, the movable part 305 limits the movement of the optical waveguide sensor chip 20 in the vertically upward direction. On the front contact surface 301a, the engagement part is arranged near the vertical center thereof. The engagement part is referred to as a protrusion 301b. The flange 603D is fitted in a recess formed by the protrusion 301b and the front contact surface 301a. Thereby, the movable part 305 limits the movement of the optical waveguide sensor chip 20 in the vertically upward direction.

When the optical waveguide sensor chip 20 is provided with a flange (the flange 603C, the flange 603D) on at least one of the side surfaces, the first mechanism 340 is provided with an engagement part that engages with the flange in an L-shape on a corresponding surface. In this configuration, the movement in the vertically upward direction can be limited without pressing the upper surface 602 of the optical waveguide sensor chip 20. Therefore, even if the optical waveguide sensor chip 20 becomes thicker due to the reaction space 102 formed therein, with the configuration in which the flanges on the sides of the optical waveguide sensor chip 20 are pressed from above, the first mechanism 340 can be provided with the engagement part having a reduced vertical length. As a result, it is possible to reliably limit the vertically upward movement of the optical waveguide sensor chip 20 as well as to prevent damage to the engagement part.

<Second Mechanism>

The second mechanism 350 includes a second contact part 302 and a third contact part 303, which are spaced apart by a predetermined distance in the left-right direction to face each other. The second contact part 302 and the third contact part 303 correspond to an example of a side surface holder. The predetermined distance is determined according to the lateral length of the outer casing 5 in the optical waveguide sensor chip 20. Hereinafter, a surface of the second contact part 302 that faces the third contact part 303 is referred to as a right contact surface 302a. Similarly, a surface of the third contact part 303 that faces the second contact part 302 is referred to as a left contact surface 303a. The distance between the right contact surface 302a and the left contact surface 303a corresponds to the predetermined distance in the left-right direction between the second contact part 302 and the third contact part 303. The right contact surface 302a and the left contact surface 303a are flat surfaces facing each other. As the second mechanism 350 holds the optical waveguide sensor chip 20 from the right surface 604R and the left surface 604L, the movement of the optical waveguide sensor chip 20 is limited in the left-right direction of the attachment part 300.

The second mechanism 350 limits the movement of the optical waveguide sensor chip 20 in the vertically upward direction. The limit of the movement is achieved by the friction between the right contact surface 302a and the right surface 604R as well as the friction between the left contact surface 303a and the left surface 604L. For example, the second mechanism 350 may be provided with an engagement part to limit the movement. In this case, the optical waveguide sensor chip 20 is also provided with an engagement part configured to be engaged with the engagement part of the second mechanisms 350. If the optical waveguide sensor chip 20 is provided with an engagement part, the engagement part may be formed in the right contact surface 302a and the left contact surface 303a in the same manner as forming the first mechanism 340. For example, the optical waveguide sensor chip 20 includes a first flange in the right surface 604R and a second flange in the left surface 604L (both not illustrated). On the other hand, the right contact surface 302a and the left contact surface 303a, which are formed to be the same plane as the bottom surface 601 of the optical waveguide sensor chip 20, are provided with guide rails (not illustrated) capable of engaging with the flanges.

The first flange on the right surface 604R of the optical waveguide sensor chip 20 is inserted in a space enclosed by the guide rail on the right contact surface 302a and the holding surface 320 as the second flange on the left surface 604L is inserted in a space enclosed by the guide rail on the left contact surface 303a and the holding surface 320. In this manner, as the optical waveguide sensor chip 20 is guided by the guide rails, the operator can appropriately move the optical waveguide sensor chip 20 along the front-back direction on the holding surface 320. By the guide rails provided on the right contact surface 302a and the left contact surface 303a to hold the flanges with the holding surface 320, the movement of the optical waveguide sensor chip 20 can be limited in the vertically upward direction.

In this case, the upper surface 310 of the measurement unit 30 is provided with a recess in which the optical waveguide sensor chip 20 is fitted. The bottom surface of the recess serves as the holding surface 320. The details are described below in the modifications of the embodiment.

<Holding Surface>

The holding surface 320 is part of the upper surface 310 enclosed by the first mechanism 340 and the second mechanism 350. That is, the holding surface 320 abuts on the movable surface 305a at the back edge, and abuts on the front contact surface 301a at the front edge. The right edge abuts on the right contact surface 302a, while the left edge abuts on the left contact surface 303a. The bottom surface 601 of the optical waveguide sensor chip 20 is held by the holding surface 320. The holding surface 320 limits the movement of the optical waveguide sensor chip 20 in the vertically upward direction.

The holding surface 320 is made of dark colored material to reduce the influence of incident light that enters the optical waveguide sensor chip 20 from the outside and stray light from the inside. Although at least the holding surface 320 needs to be dark colored in the attachment part 300, other part of the attachment part 300 may also be dark colored. The other part includes, for example, the first contact part 301, the second contact part 302, the third contact part 303, the movable part 305, and the like.

<Light Exit, Light Entrance>

A light exit 51b and a light entrance 52b are windows formed in the holding surface 320. The light exit 51b corresponds to an example of a first window, while the light entrance 52b corresponds to an example of a second window. When the optical waveguide sensor chip 20 is mounted on the attachment part 300, the light exit 51b transmits light emitted from a light source 51a (described later) toward the optical waveguide sensor chip 20, and the light entrance 52b transmits light emitted from the optical waveguide sensor chip 20. The light exit 51b constitutes part of a light generator 51 (described later). The light entrance 52b constitutes part of a light receiver 52 (described later).

The light exit 51b and the light entrance 52b are located, for example, at the same distance from the center line extending along the front-back direction of the holding surface 320. In this embodiment, the direction in which light is wave-guided by the optical waveguide sensor chip 20 is the lateral direction of the optical waveguide sensor chip 20, and therefore, the light exit 51b and the light entrance 52b are arranged in parallel in the left-right direction of the measurement unit 30. In this case, the light exit 51b and the light entrance 52b may be located in any positions in the front-back direction. For example, the center of the light exit 51b and the light entrance 52b in the front-back direction is located in front of the center of the right contact surface 302a in the front-back direction.

For another example, the direction in which light is wave-guided by the optical waveguide sensor chip 20 may be the longitudinal direction of the optical waveguide sensor chip 20. In this case, the light exit 51b and the light entrance 52b are arranged on the holding surface 320 in parallel in the front-back direction.

<Detection Switch>

The holding surface 320 is provided with a first detection switch 90a and a second detection switch 90b in a pair. The first detection switch 90a and the second detection switch 90b are an example of a contact sensor that detects whether the optical waveguide sensor chip 20 is mounted properly. The first detection switch 90a and the second detection switch 90b are located in an area between the positions of the light exit 51b and the light entrance 52b and the position of the front contact surface 301a. For example, the first detection switch 90a and the second detection switch 90b are arranged in positions that lie on a straight line along the left-right direction. In addition, for example, the first detection switch 90a and the second detection switch 90b are arranged in positions line symmetrical with respect to the center line of the holding surface 320. Note that the first detection switch 90a and the second detection switch 90b need not necessarily be located line symmetrically.

In this case, the first detection switch 90a corresponds to an example of a first detection sensor, and the second detection switch 90b corresponds to an example of a second detection sensor. The first detection switch 90a and the second detection switch 90b are button switches movable in the vertical direction. Examples of the button switches include mechanical detection switches. The mechanical detection switch is provided with a predetermined detection position in the vertical direction. For example, when pressed down to be lower than the predetermined detection position, the mechanical detection switch generates a detection signal.

When the optical waveguide sensor chip 20 is properly mounted on the attachment part 300, the bottom surface 601 comes in contact with the holding surface 320. Accordingly, both the first detection switch 90*a* and the second detection switch 90*b* are pressed by the bottom surface 601 to the predetermined detection position. Thus, the first detection switch 90*a* and the second detection switch 90*b* pressed down to the predetermined detection position each generate a detection signal. That is, the measurement unit 30 can determine that the mounting is proper based on the detection signals generated by both the first detection switch 90*a* and the second detection switch 90*b*. Besides, if either or both the first detection switch 90*a* and the second detection switch 90*b* do not generate a detection signal, the measurement unit 30 can determine that the mounting is improper.

For example, the improper mounting indicates that the optical waveguide sensor chip 20 is mounted in such a state where the bottom surface 601 is floating above the holding surface 320 and is at an angle with respect to the holding surface 320. In this case, either one or both of the first detection switch 90*a* and the second detection switch 90*b* are not pressed down to the predetermined detection position. Accordingly, either one or both of the first detection switch 90*a* and the second detection switch 90*b* do not generate a detection signal. With this, the measurement unit 30 can detect the improper mounting of the optical waveguide sensor chip 20. This determination is described in detail below in a description of a determination unit 85.

The first detection switch 90*a* and the second detection switch 90*b* may be located in positions where they are spaced apart from each other by the maximum possible distance in the left-right direction on the holding surface 320. The positions are near the right contact surface 302*a* and the left contact surface 303*a*, for example. Specifically, the first detection switch 90*a* may be located near the right contact surface 302*a*, while the second detection switch 90*b* may be located near the left contact surface 303*a*. With this, the detection switches can detect the positions of the lateral edges of the optical waveguide sensor chip 20. Thus, it is possible to detect the inclination of the optical waveguide sensor chip 20 on the holding surface 320 in the vertical direction in the lateral direction of the optical waveguide sensor chip 20 with accuracy.

Further, the first detection switch 90*a* and the second detection switch 90*b* can be located near the front contact surface 301*a*. With this, the detection switches can detect the position of the front edge of the optical waveguide sensor chip 20. Thus, it is possible to detect the vertical inclination of the optical waveguide sensor chip 20 in the longitudinal direction thereof on the holding surface 320 with accuracy.

In other words, preferably, the first detection switch 90*a* and the second detection switch 90*b* are located near the front contact surface 301*a*, and also the first detection switch 90*a* is located near the right contact surface 302*a*, while the second detection switch 90*b* is located near the left contact surface 303*a*.

To detect whether the optical waveguide sensor chip 20 is mounted properly by the first detection switch 90*a* and the second detection switch 90*b*, preferably, the protrusion 305*b* as the aforementioned engagement part is arranged at least on the movable surface 305*a*. In this case, the back surface 603B of the optical waveguide sensor chip 20 is provided with a protrusion, i.e., the flange 603C. The optical waveguide sensor chip 20 may be mounted on the measurement unit 30, for example, in a manner as follows.

(How to Mount)

The optical waveguide sensor chip 20 is placed on the attachment part 300 as being inclined such that the front surface 603F faces the holding surface 320. Next, the flange 603C (protrusion) is fitted in the recess formed by the movable surface 305*a* and the protrusion 305*b*. The optical waveguide sensor chip 20 is moved in the direction from the front thereof to the back in the longitudinal direction, and thereby the movable part 305 is pushed in the opposite direction to the biasing force exerted by the elastic parts 306*a* and 306*b*. Accordingly, the length of the holding surface 320 in the front-back direction becomes longer than the longitudinal length of the optical waveguide sensor chip 20. At this time, the bottom surface 601 comes in contact with the holding surface 320. With this, the bottom surface 601 presses the first detection switch 90*a* and the second detection switch 90*b* down to the predetermined detection position. Then, while the bottom surface 601 is being in contact with the holding surface 320, the movable part 305 is pushed in the opposite direction.

The movable part 305 thus pushed abuts on the stopper 307 and thereby its movement is stopped. At this time, the front surface 603F of the optical waveguide sensor chip 20 is located between the front edge and the back edge of the first detection switch 90*a* and the second detection switch 90*b* in the front-back direction of the holding surface 320. That is, at this time, the front surface 603F is located in the front-back direction in a position included in the width of the upper projection surface of each of the first detection switch 90*a* and the second detection switch 90*b*.

The first detection switch 90*a* and the second detection switch 90*b* are arranged in the positions as described above taking into account the longitudinal length of the optical waveguide sensor chip 20 and the backward movable distance of the movable part 305. Thus, when the first detection switch 90*a* and the second detection switch 90*b* are pressed down to the predetermined detection position, the operator can check them from above. This is at a stage prior to the state where the optical waveguide sensor chip 20 is ready to be mounted properly. Accordingly, the operator can check whether the optical waveguide sensor chip 20 can be mounted properly at the prior stage. As the pushing force applied to the movable part 305 is released in this state, the back surface 603B of the optical waveguide sensor chip 20 comes in contact with the front contact surface 301*a*. In this manner, the operator can mount the optical waveguide sensor chip 20 on the attachment part 300 properly.

The first detection switch 90*a* and the second detection switch 90*b* are made of, for example, bright colored material such as white material. Since the holding surface 320 is made of dark colored material such as black material, the first detection switch 90*a* and the second detection switch 90*b* can be easily visually checked. Accordingly, the operator can use the first detection switch 90*a* and the second detection switch 90*b* as targets to mount the optical waveguide sensor chip 20 on the attachment part 300. This enables the operator to easily figure out the position of the attachment part 300. In addition, as a direction in which the optical waveguide sensor chip 20 is pushed to be mounted is perpendicular to the array direction of the first detection switch 90*a* and the second detection switch 90*b*, the operator can easily figure out the pushing and the like. Further, the first detection switch 90*a* may be located near the second contact part 302, while the second detection switch 90*b* may be located near the third contact part 303. In this case, by visually checking the locations of the first detection switch 90*a* and the second detection switch 90*b*, the operator can easily figure out that the locations correspond to the lateral ends of the optical waveguide sensor chip 20.

Figure 6:
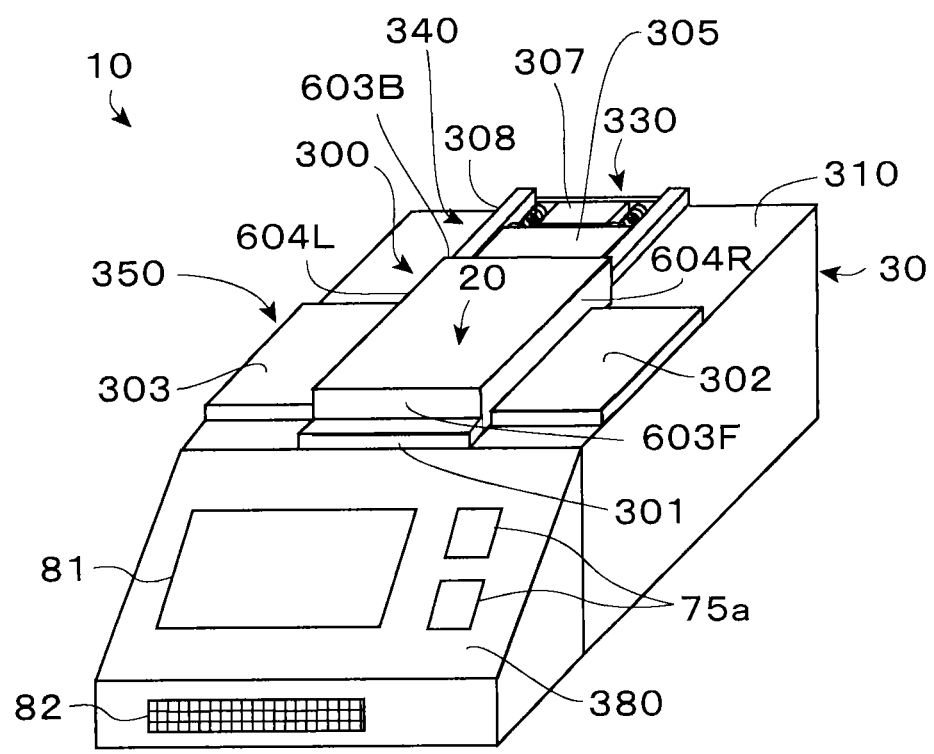
FIG. 6 is a perspective view of an example of the measurement unit equipped with the optical waveguide sensor chip.

FIG. 6 is a perspective view of an example of the measurement unit 30 properly equipped with the optical waveguide sensor chip 20. As illustrated in FIG. 6, the first mechanism 340 holds the optical waveguide sensor chip 20 from the front surface 603F and the back surface 603B. Meanwhile, the second mechanism 350 holds the optical waveguide sensor chip 20 from the right surface 604R and the left surface 604L. That is, the optical waveguide sensor chip 20 is held by the first mechanism 340 and the second mechanism 350 that surround its side surfaces. On this occasion, both the first detection switch 90a and the second detection switch 90b generate a detection signals. The detection signal indicates that the bottom surface 601 is in contact with the holding surface 320 and the surfaces are parallel to each other.

As described above, the the intensity of light output from the optical waveguide sensor chip 20 corresponds to the amount of the solid dispersion elements 9 present in the sensing area 103. However, the amount of the solid dispersion elements 9 does not always coincide with the amount of the antigen 14. In other words, in the sensing area 103, there may be the solid dispersion elements 9 that are not bound to the sensing surface 101 via the antigen 14. Such the solid dispersion elements 9 may be, for example, those that specifically adsorb onto the sensing surface 101 due to intermolecular force, hydrophobic interaction, or the like, or those that are floating in the vicinity of the sensing area 103. The solid dispersion elements 9 that are not bound to the sensing surface 101 via the antigen 14 may cause an error in measuring the amount of the antigen 14 retained in the reaction space 102. Therefore, the solid dispersion elements 9 that provide an error factor need to be selectively removed. For example, the solid dispersion elements 9 retained in the reaction space 102 include the magnetic microparticles 12 that carry the second antibodies 13. By applying a magnetic field to the reaction space 102, the measurement unit 30 generates a force due to the magnetic field for the solid dispersion elements 9, thereby selectively removing the solid dispersion elements 9.

Figure 7:
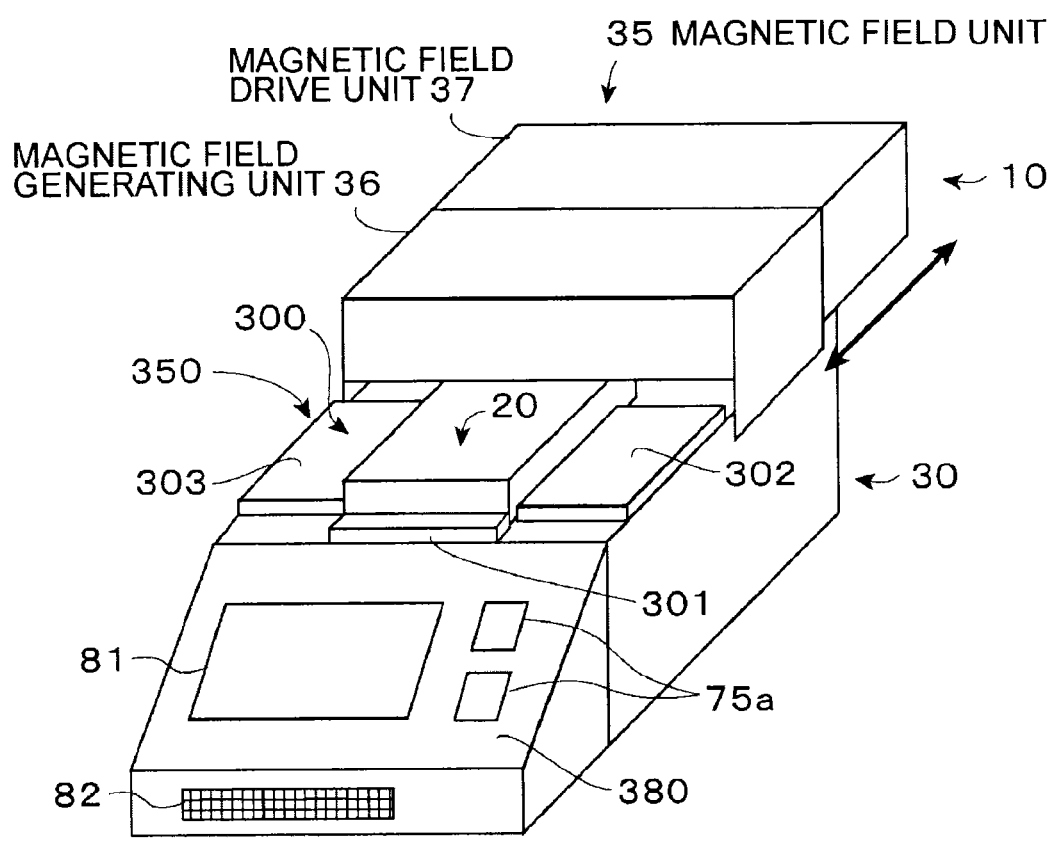
FIG. 7 is a perspective view of another example of the measurement unit equipped with the optical waveguide sensor chip.

FIG. 7 is a perspective view of another example of the measurement unit 30 properly equipped with the optical waveguide sensor chip 20. As illustrated in FIG. 7, the measurement unit 30 includes a magnetic field unit 35. The magnetic field unit 35 includes a built-in device corresponding to a magnetic field generator 21 and a drive controller 40. The magnetic field unit 35 is formed in the shape of a box and arranged above the upper surface 310 of the measurement unit 30. The magnetic field unit 35 includes a magnetic field generating unit 36 and a magnetic field drive unit 37. In the magnetic field unit 35, the magnetic field generating unit 36 is located on the front side. The magnetic field generating unit 36 includes a built-in device corresponding to an upper magnetic field applicator 21a that generates a magnetic field directed vertically upward. In the magnetic field unit 35, the magnetic field drive unit 37 is located on the rear side. The magnetic field drive unit 37 includes a built-in device configured to be capable of controlling and driving the built-in device in the magnetic field generating unit 36 corresponding to the upper magnetic field applicator 21a.

Figure 8:
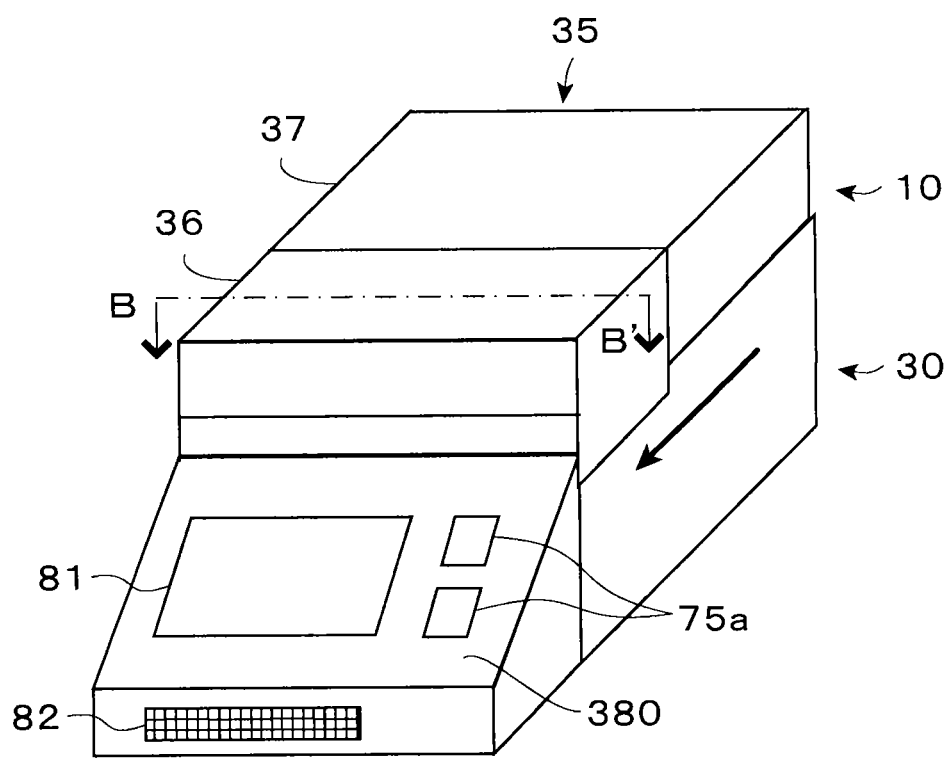
FIG. 8 is a perspective view of an example of the optical waveguide measurement system in a state ready for measurement.

FIG. 8 is a perspective view of an example of the optical waveguide measurement system 10 in a state ready for measurement. As illustrated in FIG. 8, the magnetic field unit 35 is connected to a slide mechanism of the measurement unit 30, and thereby capable of sliding backward (the first direction) and forward (a direction opposite to the first direction; −y direction). As the magnetic field unit 35 is sliding forward, the magnetic field generating unit 36 moves to above the optical waveguide sensor chip 20. With this, the built-in device of the magnetic field generating unit 36 corresponding to the upper magnetic field applicator 21a can apply a magnetic field directed vertically upward to the optical waveguide sensor chip 20. Thus, the solid dispersion elements 9 that provide an error factor can be selectively removed.

[Configuration of the Optical Waveguide Measurement System]

Figure 9:
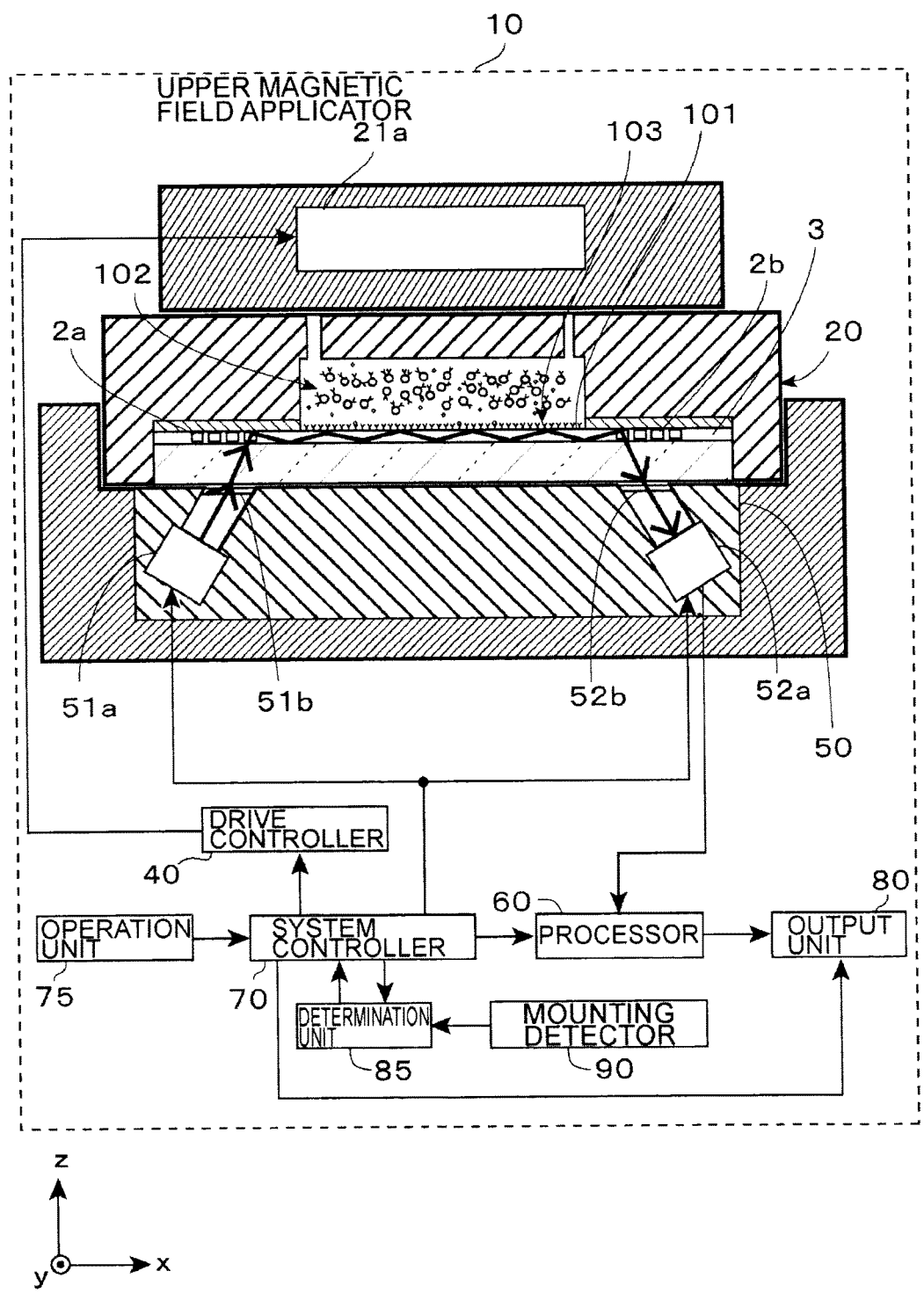
FIG. 9 is a cross-sectional view of the optical waveguide measurement system.

With reference to FIGS. 1 to 9, a description is given of the configuration of the optical waveguide measurement system 10 in which the optical waveguide sensor chip 20 is properly mounted on the measurement unit 30. FIG. 9 is a cross-sectional view of the optical waveguide measurement system 10 taken along line B-B' in FIG. 8. As well as the cross section taken along line B-B' in FIG. 8, FIG. 9 illustrates the control configuration of the measurement unit 30. The cross section corresponds to the x-y cross section of the light exit 51b and the light entrance 52b in the measurement unit 30.

As illustrated in FIGS. 1 and 9, the measurement unit 30 that constitutes the principal part of the optical waveguide measurement system 10 includes the magnetic field generator 21, the drive controller 40, the light transceiver 50, a processor 60, a system controller 70, an operation unit 75, the output unit 80, the determination unit 85, and a mounting detector 90. In the optical waveguide measurement system 10, light output from the light transceiver 50 enters the optical waveguide part 3 of the optical waveguide sensor chip 20. The light is wave-guided through the optical waveguide part 3. The light is then output from the optical waveguide part 3 to the outside, and is detected by the light transceiver 50. The optical waveguide sensor chip 20 is configured to attenuate the light propagating through the optical waveguide part 3 according to the amount of the antigen 14 retained in the reaction space 102. From information on the light detected, information can be obtained regarding the antigen 14 retained in the reaction space 102. The information regarding the antigen 14 indicates, for example, the type, amount, density, and the like of the antigen 14.

(Light Transceiver)

The light transceiver 50 includes the light generator 51 and the light receiver 52 (see FIG. 1). The light generator 51 lets the light enter the optical waveguide part 3 of the optical waveguide sensor chip 20, and be wave-guided through the optical waveguide part 3. The light receiver 52 receives the light that has been wave-guided through the optical waveguide part 3 and then output therefrom.

(Light Generator)

The light generator 51 is configured to emit light to the outside. In the measurement unit 30, the light generator 51 includes the light source 51a and the light exit 51b. The light source 51a generates light to be incident on the optical waveguide sensor chip 20. The light generated by the light source 51a travels to the light exit 51b and introduced to the optical waveguide sensor chip 20 therefrom. At this time, if the optical waveguide sensor chip 20 is mounted on the attachment part 300 properly, the incident light L1 is incident on a predetermined position of the grating 2a at the entrance. The light that has entered the optical waveguide part 3 from the light source 51a is diffracted by the grating 2a and wave-guided through the optical waveguide part 3.

The incident light L1 is diffracted a predetermined number of times by the grating 2a, and thereby is wave-guided properly in the optical waveguide part 3. The predetermined number of times may be, for example, once. Therefore, light beams that enter the optical waveguide part 3 are not allowed to be incident on any position of the grating 2a but required to be incident on a predetermined position at a predetermined angle. As described above, the grating 2a at the entrance is formed of a plurality of gratings having a predetermined pitch dimension, which are arranged at predetermined intervals in the longitudinal direction of the window 610 (x direction). The predetermined position is the position of one of the gratings at the longitudinal edge of the grating 2a when the predetermined number of times is once.

The position where the incident light L1 is incident on the grating 2a may be set to an arbitrary range in which the light is properly wave-guided in the optical waveguide part 3. When the light is totally reflected appropriate number of times on a surface of the optical waveguide part 3 corresponding to the sensing surface 101, it means that the light is properly wave-guided. The number of times is set in advance. The surface of the optical waveguide part 3 corresponding to the sensing surface 101 may sometimes be referred to as "sensing corresponding surface".

As described above, when the light is totally reflected on the sensing corresponding surface, near-field light is generated in the sensing surface 101 at a position corresponding to where the light is totally reflected. Due to the fact that the near-field light is affected depending on the state of the reaction space 102, the light wave-guided through the optical waveguide part 3 is attenuated. The measurement unit 30 receives the attenuated light and obtains the degree of the attenuation, thereby acquiring the density and the like of a test article in the reaction space 102. By setting the number of total reflections on the sensing corresponding surface to an appropriate range in advance, the near-field light generated in the reaction space 102 can be in the size of the set value. The density and the like of the test article in the reaction space 102 are sensed with the near-field light, and thus the density and the like can be measured appropriately.

On the other hand, if the light is totally reflected on the sensing corresponding surface more than appropriate times, the light is attenuated more times. As a result, the light wave-guided through the optical waveguide part 3 is attenuated more than originally required according to the mount of the antigen 14. Consequently, for example, a value higher than the actual density of the test article in the reaction space 102 is obtained by the measurement. In this manner, if the number of total reflections on the sensing corresponding surface falls out of the range set in advance, the measurement unit 30 cannot properly measure the density and the like of the test article in the reaction space 102. For these reasons, the light to be incident on the grating 2a is required to enter the optical waveguide part 3 in a position and at an angle to be properly wave-guided.

The light emitted from the light source 51a is, for example, beams of LED light, laser light, or the like. The light is continuous light with an intensity that substantially does not vary in the time-series. When the light source 51a emits light beams, if the beam width is narrower than the width of the optical waveguide part 3, every single beam of light emitted from the light source 51a can enter the optical waveguide part 3. Thus, the intensity of light emitted from the light source 51a can be regarded as that of the incident light L1 (input light) on the optical waveguide part 3. Examples of the light source 51a include a variety of light-emitting elements. Examples of the light-emitting elements include light emitting diodes (LEDs), laser diodes (LDs), and the like.

<Light Receiver>

As illustrated in FIG. 9, the light receiver 52 receives light incident from the outside. The light receiver 52 includes a light receiving device 52a and the light entrance 52b. The light receiver 52 is arranged at a position where it can receive output light L2 emitted toward the outside from the grating 2b at the exit when the optical waveguide sensor chip 20 is mounted properly on the measurement unit 30. The light receiving device 52a includes, for example, a light receiving element (photosensor) such as a photodiode. The light receiving element is arranged at a position where it can receive light emitted through the grating 2b at the exit. When the light source 51a emits laser light, the light receiving device 52a includes, as the light receiving element, the one having a width larger than the beam width of light output from the optical waveguide part 3. By using such a light receiving element, every single beam of light from the optical waveguide part 3 can be received. Thus, the intensity of light received by the light receiving device 52a can be regarded as that of light output from the optical waveguide part 3, i.e., the intensity of the output light L2. The light receiver 52 feeds the processor 60 with information on the output light L2 received by the light receiving device 52a. That is, having received the incident light L1 from the light source 51a, the optical waveguide sensor chip 20 performs sensing in the sensing area 103, and outputs light that includes sensing information as the output light L2 to the light receiving device 52a.

(System Controller)

The system controller 70 is a system control circuit configured to control each of the light transceiver 50, the drive controller 40, the processor 60, the determination unit 85, and the output unit 80 for the overall control of the optical waveguide measurement system 10. The system control circuit includes combinations of various electrical elements and conductors for implementing required functions. The operation unit 75 is used to feed the system controller 70 with a variety of command signals.

(Processor)

Having received the information on the output light L2 received by the light receiver 52, the processor 60 performs processing on the information of the light. Through the processing the processor 60 can acquire information such as, for example, the intensity, wavelength, phase, and the like of the light received by the light receiver 52. Besides, the processor 60 obtains, for example, the intensity of light output from the light generator 51 to the optical waveguide sensor chip 20 as information on the input light to the optical waveguide sensor chip 20. Thus, the processor 60 can also generate information indicating the ratio of intensity between light incident on the optical waveguide sensor chip 20 and a response signal output therefrom. Further, the processor 60 may process the intensity of the output light L2 that has been received with time to obtain time-series information on the intensity of the output light L2. The variety of information generated by the processor 60 is output to, for example, the display 81 or the like as the output unit 80. For example, the processor 60 is an optical information processing circuit including combinations of various electrical elements and conductors for implementing the functions of acquiring, processing, generating, and outputting information related to light generated by the light generator 51 and that received by the light receiver 52.

<Magnetic Field Generator>

The magnetic field generator 21 applies a magnetic field to the reaction space 102, thereby generating a force with respect to the solid dispersion elements 9 (the magnetic microparticles 12) retained in the reaction space 102. The magnetic field generator 21 generates a magnetic flux vertically penetrating through the reaction space 102. The magnetic field generator 21 may be formed of, for example, a permanent magnet, an electromagnet, or a combination of them. For example, the magnetic field generator 21 may include an upper magnetic field applicator capable of generating an upward magnetic flux that vertically penetrates through the reaction space 102 and a lower magnetic field applicator capable of generating a downward magnetic flux that vertically penetrates through the reaction space 102.

<<Upper Magnetic Field Applicator>>

As illustrated in FIG. 9, the measurement unit 30 includes the upper magnetic field applicator 21a as part of the magnetic field generator 21. The upper magnetic field applicator 21a is located above the optical waveguide sensor chip 20. A force is applied to the solid dispersion elements 9 (the magnetic microparticles 12) contained in the reaction space 102 in the vertically upward direction due to the intensity of a magnetic field generated by the upper magnetic field applicator 21a. The solid dispersion elements 9 are moved vertically upward by the force applied in the vertically upward direction. In this case, by setting the force applied to the solid dispersion elements 9 to be smaller than the binding force between the first antibodies 6 and the antigen 14 as well as that between the second antibodies 13 and the antigen 14, the solid dispersion elements 9 that provide an error factor can be selectively separated from the sensing area 103.

For example, if formed of a permanent magnet, the upper magnetic field applicator 21a is arranged such that one end thereof, which is a pole of the magnet, faces the surface of the optical waveguide part 3 that forms the reaction space 102. Besides, the upper magnetic field applicator 21a may be formed of a plurality of permanent magnets arranged in parallel with their poles directed to the same direction, or may be formed of rod-shaped coils. In this case, the coil is arranged such that one end thereof faces the surface of the optical waveguide part 3 that forms the reaction space 102. When the upper magnetic field applicator 21a applies a magnetic field to the reaction space 102, the same amount of electric current flows through the rod-shaped coils in the same direction.

The measurement unit 30 may be provided with a lower magnetic field applicator (not illustrated). In this case, the lower magnetic field applicator may be located opposite the upper magnetic field applicator 21a across the optical waveguide sensor chip 20.

<Drive Controller>

The drive controller 40 includes a controller 41 and a driver 42. The drive controller 40 controls and drives each of the constituent elements of the measurement unit 30, such as the upper magnetic field applicator 21a.

<<Controller>>

The controller 41 issues an instruction to various types of drive units in the driver 42 to control the driving of the constituent elements of the measurement unit 30 corresponding to the drive units.

<<Driver>>

Upon receipt of an instruction from the controller 41, the driver 42 drives the upper magnetic field applicator 21a. When driven by the driver 42, as described above, the upper magnetic field applicator 21a generates a magnetic field directed vertically upward in the reaction space 102. The magnetic force applied to the solid dispersion elements 9 in the reaction space 102 due to the magnetic field is smaller than the binding force between the first antibodies 6 and the antigen 14 as well as that between the second antibodies 13 and the antigen 14, and is sufficient to selectively separate the solid dispersion elements 9 that provide an error factor from the sensing area 103. In this case, the solid dispersion elements 9 are separated vertically upward from the sensing area 103 by, for example, a few hundred nanometers. Thus, the solid dispersion elements 9 that provide an error factor can be selectively separated from the sensing area 103 without disbinding the solid dispersion elements 9 that specifically binds to the sensing surface 101 via the antigen 14.

The mounting detector 90 detects the mounting of the optical waveguide sensor chip 20 on the measurement unit 30. The mounting detector 90 includes the first detection switch 90a and the second detection switch 90b. The first detection switch 90a and the second detection switch 90b each output a detection signal to the determination unit 85. The mounting detector 90 may further include a detection switch in addition to the first detection switch 90a and the second detection switch 90b.

<Determination Unit>

Upon receipt of a detection signal from the mounting detector 90, the determination unit 85 determines whether the optical waveguide sensor chip 20 is mounted properly on the measurement unit 30. Having received a detection signal from both the first detection switch 90a and the second detection switch 90b, the determination unit 85 determines that the optical waveguide sensor chip 20 is mounted properly on the measurement unit 30. Otherwise, the determination unit 85 determines that the optical waveguide sensor chip 20 is mounted improperly.

Assuming that the determination unit 85 has been receiving a detection signal from both the first detection switch 90a and the second detection switch 90b, if receiving no signal from either or both of them after input of an instruction for the end of measurement, the determination unit 85 determines that the optical waveguide sensor chip 20 is removed from the measurement unit 30. Then, the determination unit 85 is placed in standby for the next mounting of the optical waveguide sensor chip 20. Besides, the determination unit 85 is capable of monitoring a detection signal from both the first detection switch 90a and the second detection switch 90b during a measurement. Specifically, if, having been receiving a detection signal from both the first detection switch 90a and the second detection switch 90b after determining that the optical waveguide sensor chip 20 is mounted properly and before receiving an instruction for the end of measurement, receiving no signal from at least either one of them, the determination unit 85 determines that an error occurs in the mounting state of the optical waveguide sensor chip 20. Then, for example, the determination unit 85 outputs the determination result to the system controller 70. In response to the determination result, the system controller 70 controls the output unit 80. For example, the output unit 80 controls the notification unit 82 to provide a notification of the change in the mounting state to the outside. For another example, the output unit 80 may control the display 81 to display information indicating the change in the mounting state on the display screen. The determination unit 85 is a determination circuit that includes combinations of various electrical elements and conductors for implementing the function of determination based on the contact state of the chip with the placement surface where the bottom of the chip is placed. The determination circuit receives the output of the contact sensor.

[Operation of the Optical Waveguide Measurement System]

Described below is an example in which the optical waveguide measurement system 10 measures the density of the antigen 14 retained in the reaction space 102. The description is made referring to FIGS. 1 to 9 as appropriate.

The antigen 14 and the solid dispersion elements 9 retained in the reaction space 102 spontaneously precipitate therein due to the gravity. On this occasion, antibody-antigen reaction occurs between the antigen 14 and the second antibodies 13 that constitute the solid dispersion elements 9. Due to the antibody-antigen reaction, the antigen 14 and the solid dispersion elements 9 are bound together. The antigen 14 precipitates to the sensing surface 101 that retains the first antibodies 6, and reacts with the first antibodies 6 through antigen-antibody reaction. Due to the antibody-antigen reaction, the sensing surface 101 and the antigen 14 are bound together. In addition, the antigen 14 that have bound to the sensing surface 101 further binds to the solid dispersion elements 9, and also the antigen 14 that have bound to the solid dispersion elements 9 further binds to the sensing surface 101. Thereby, the solid dispersion elements 9 and the sensing surface 101 are bound together via the antigen 14. With this, the solid dispersion elements 9 are retained in the sensing area 103. In this state, the light generator 51 emits light to the optical waveguide part 3. While the light is being wave-guided through the optical waveguide part 3 as being appropriately diffracted by the grating 2a at the entrance, near-field light is generated in the sensing area 103 due to the waveguiding.

The near-field light is dispersed and absorbed by the solid dispersion elements 9, and accordingly, the intensity of light that is wave-guided through the optical waveguide part 3 is attenuated. The light thus attenuated is appropriately diffracted by the grating 2b at the exit to be incident on the light receiver 52. The light receiver 52 feeds the processor 60 with information on the light.

The processor 60 obtains the degree of the attenuation of the light based on the intensity of the light received by the light receiver 52 and its original intensity. Here, the intensity of the light received by the light receiver 52 corresponds to the amount of the solid dispersion elements 9 present in the sensing area 103.

Although the measurement object is the solid dispersion elements 9 that bind to the sensing surface 101 via the antigen 14, the solid dispersion elements 9 other than them are also present in the sensing area 103, thereby causing an error in the measurement. This is because the solid dispersion elements 9 spontaneously precipitate and accumulate in the sensing area 103. Since the solid dispersion elements 9 contain the magnetic microparticles 12, when the upper magnetic field applicator 21a applies an upward magnetic field to the reaction space 102, a vertically upward force is applied to the solid dispersion elements 9. Thereby, the solid dispersion elements 9 that do not bind to the sensing surface 101 are separated away from the sensing area 103. In this manner, the solid dispersion elements 9 that provide an error factor can be selectively moved out of the sensing area 103.

Even after the solid dispersion elements 9 that do not bind to the sensing surface 101 have been selectively moved out, the measurement unit 30 outputs the intensity of the light received by the light receiver 52 to the processor 60. The intensity of the light is light intensity corresponding to the density of the antigen 14. The processor 60 calculates the attenuation of the light intensity by, for example, comparing the light intensity corresponding to the density of the antigen 14 with light intensity immediately after the start of the measurement.

The processor 60 calculates the density of the antigen 14 retained in the reaction space 102 based on the attenuation of the light intensity. The processor 60 feeds the output unit 80 with the calculation result to output it. With reference to the calculation result output by the output unit 80, the operator can recognize the density (amount) of the antigen 14 retained in the reaction space 102.

[Mounting of the Optical Waveguide Sensor Chip on the Measurement Unit]

Figure 10:
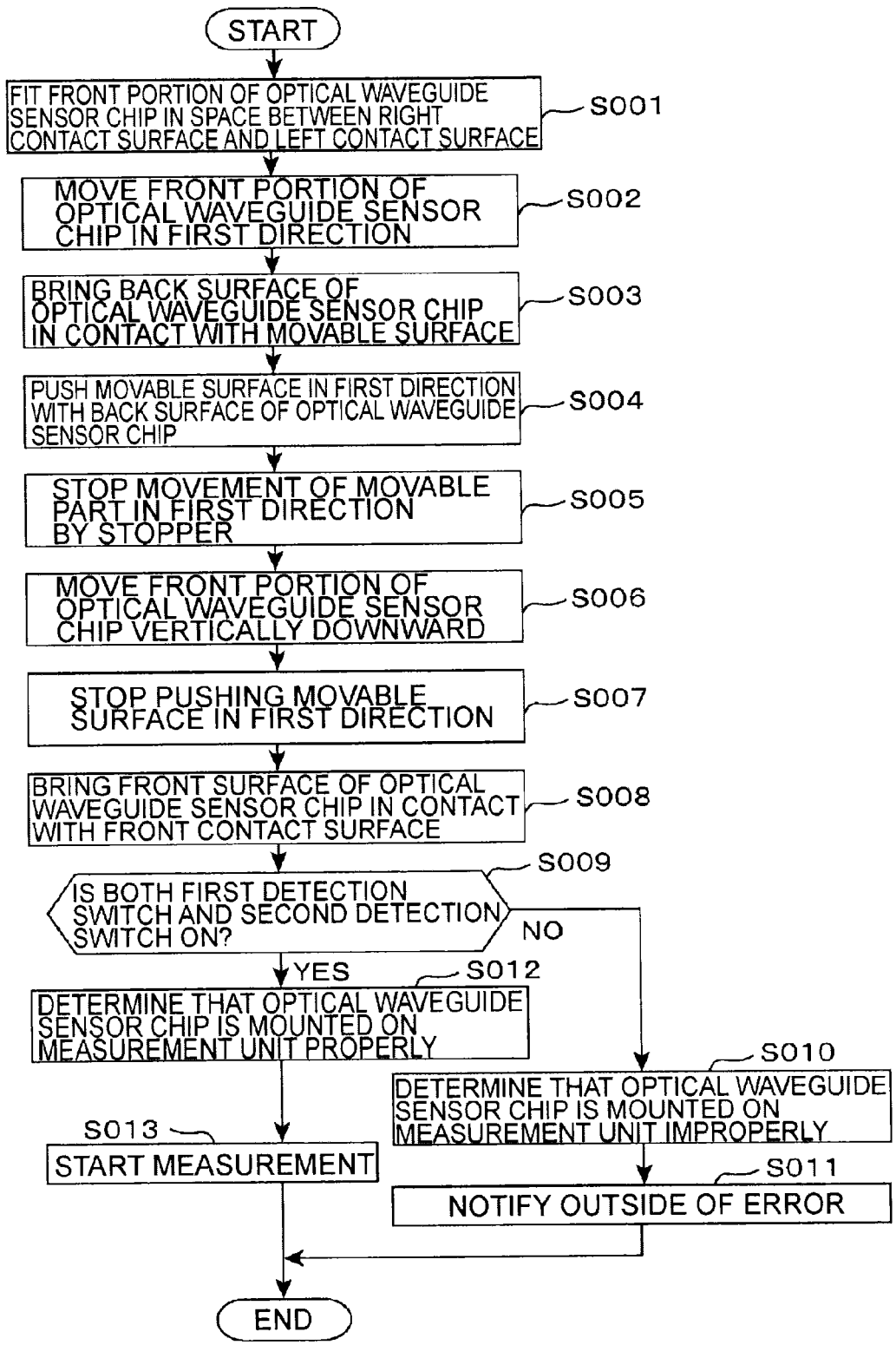
FIG. 10 is a flowchart of a procedure for mounting the optical waveguide sensor chip on the measurement unit.

In the following, a description is given of how to mount the optical waveguide sensor chip on the measurement unit. FIG. 10 is a flowchart of a procedure for mounting the optical waveguide sensor chip 20 on the measurement unit 30. FIG. 10 illustrates a procedure for mounting the optical waveguide sensor chip 20 on the attachment part 300 of the measurement unit 30 illustrated in FIGS. 4 to 9. The description is made referring to FIGS. 4 to 9 as appropriate.

As illustrated in FIG. 10, first, the front portion of the optical waveguide sensor chip 20 is fitted in a space between the right contact surface 302a and the left contact surface 303a (step S001). The operator moves the optical waveguide sensor chip 20 backward along the right contact surface 302a and the left contact surface 303a while holding the front part of the optical waveguide sensor chip 20 (step S002).

When the holding surface 320 is exposed sufficiently for the bottom surface 601 to be mounted thereon, the operator moves the optical waveguide sensor chip 20 down such that the corner formed at the boundary between the back surface 603B and the bottom surface 601 is sliding on the holding surface 320 to bring the bottom surface 601 in contact with the holding surface 320. At this time, the optical waveguide sensor chip 20 is moved down so that the right surface 604R comes almost in contact with the right contact surface 302a and the left surface 604L comes almost in contact with the left contact surface 303a. The operator brings the back surface 603B in contact with the movable surface 305a while inclining the optical waveguide sensor chip 20 (step S003).

The operator further moves the optical waveguide sensor chip 20 backward in the state of step S003, thereby pushing the movable surface 305a backward with the back surface 603B (step S004).

The stopper 307 stops the backward movement of the movable part 305 (step S005). At this time, the front portion of the optical waveguide sensor chip 20 is settled down such that the bottom surface 601 of the optical waveguide sensor chip 20 is in contact with the holding surface 320, and the back surface 603B is in contact with the movable surface 305a (step S006). The operator performs this while pushing the movable surface 305a backward. When the optical waveguide sensor chip 20 is brought in contact with the holding surface 320 properly, the bottom surface 601 of the optical waveguide sensor chip 20 comes in contact with the holding surface 320. As a result, the first detection switch 90a and the second detection switch 90b are pressed down on the holding surface 320 by the corner in the boundary between the front surface 603F and the bottom surface 601 of the optical waveguide sensor chip 20.

The front portion of the optical waveguide sensor chip 20 may be settled down before the stopper 307 stops the backward movement of the movable part 305. In other words, in step S004, as long as the movable part 305 has been moved backward by a distance sufficient for the placement of the bottom surface 601, the optical waveguide sensor chip 20 can be moved down.

Figure 11:
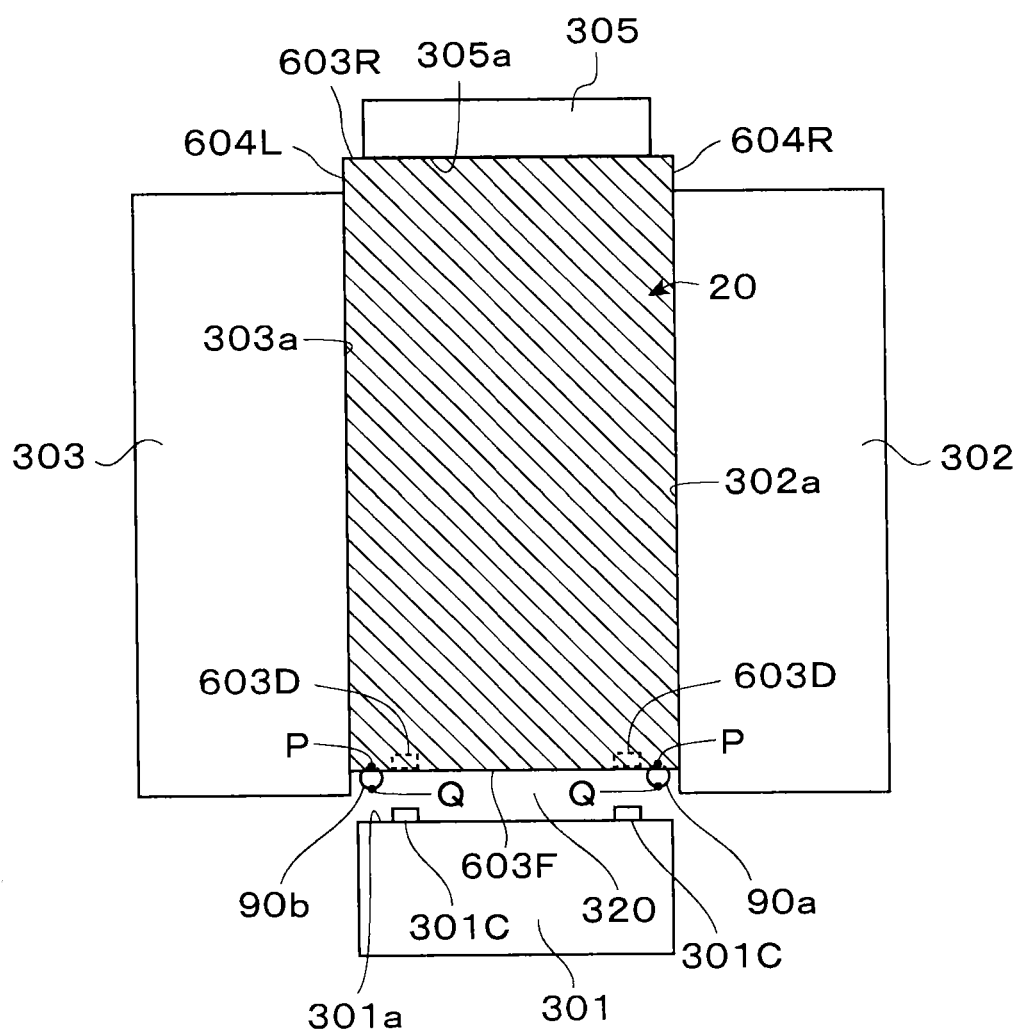
FIG. 11 is a top view of a first detection switch and a second detection switch partially exposed from the vicinity of the back of the optical waveguide sensor chip.

FIG. 11 is a top view of the first detection switch 90a and the second detection switch 90b partially exposed from the vicinity of the front surface 603F of the optical waveguide sensor chip 20. Unexposed part of the first detection switch 90a and the second detection switch 90b is in contact with the bottom surface 601.

That is, in this state, positions P of the back ends of the first detection switch 90a and the second detection switch 90b are located backward from the front surface 603F of the optical waveguide sensor chip 20 and below the bottom surface 601. On the other hand, positions Q of the front ends of the first detection switch 90a and the second detection switch 90b are located forward from the front surface 603F of the optical waveguide sensor chip 20 and exposed. This enables the front surface 603F not to be caught by the first detection switch 90a and the second detection switch 90b when the optical waveguide sensor chip 20 slides forward.

Further, in this state, by visually checking the positional relationship between the front surface 603F and the first detection switch 90a and the second detection switch 90b, the operator can determine whether the optical waveguide sensor chip 20 is in a state where it can be mounted properly.

Next, the operator stops pushing the movable surface 305a backward while keeping the bottom surface 601 in contact with the holding surface 320 (step S007). As a forward biasing force is applied to the movable part 305 by the elastic parts 306a and 306b, the optical waveguide sensor chip 20 slides forward. Thereby, the front surface 603F of the optical waveguide sensor chip 20 comes in contact with the front contact surface 301a (step S008). Thus, the optical waveguide sensor chip 20 is held by the first mechanism 340. In addition, by step S007, engagement claws 301C arranged on the front contact surface 301a come in contact with the upper surface 602 of the optical waveguide sensor chip 20. In this case, by step S007, the flange 603D on the front surface 603F fits in a groove (engagement part) formed below the engagement claws 301C. This limits the upward movement of the front portion of the optical waveguide sensor chip 20. Similarly, the flange 603C on the back surface 603B fits in a groove (engagement part) formed below the protrusion 305b of the movable surface 305a. This limits the upward movement of the rear portion of the optical waveguide sensor chip 20. With such engagement parts, the upward positional shift of the entire optical waveguide sensor chip 20 can be prevented.

On completion of the mounting procedure, the determination unit 85 determines whether a detection signal is received from both the first detection switch 90a and the second detection switch 90b. Having received a detection signal from both the first detection switch 90a and the second detection switch 90b (Yes in step S009), the determination unit 85 determines that the optical waveguide sensor chip 20 is mounted properly on the measurement unit 30. When it is determined that the optical waveguide sensor chip 20 is mounted properly, the optical waveguide measurement system 10 becomes ready for a measurement. In response to a predetermined trigger to start measurement, the optical waveguide measurement system 10 starts the measurement (step S013). The measurement start trigger may be, for example, the acquisition of the determination result as to the proper mounting by the determination unit 85, or it may be an instruction input automatically or manually. Examples of the instruction input manually include an instruction to start measurement, an identification process (barcode reading, etc.) for the optical waveguide sensor chip 20, and the like.

On the other hand, having received no signal from either or both the first detection switch 90a and the second detection switch 90b (No in step S009), the determination unit 85 determines that the optical waveguide sensor chip 20 is mounted on the measurement unit 30 improperly (step S010). In response to the determination result, the system controller 70 controls the notification unit 82 to notify the outside of the error (step S011).

An example of the error is described below. There may be a case where the bottom surface 601 of the optical waveguide sensor chip 20 runs on the second contact part 302, and the flange 603D of the front surface 603F engages with the engagement claws 301C of the front contact surface 301a. In this case, the optical waveguide sensor chip 20 is mounted at an angle with respect to the holding surface 320, and the mounting is actually improper; however, the optical waveguide sensor chip 20 seemingly appears to be mounted properly. On such an occasion, the first detection switch 90a on the right is not pressed down, resulting in an error notification. The operator can notice the error by the error notification and thus perform the mounting procedure again.

When the measurement is completed while the optical waveguide sensor chip 20 is mounted on the measurement unit 30 properly, the series of processes ends. On the other hand, if the optical waveguide sensor chip 20 is mounted on the measurement unit 30 improperly, the series of processes ends, for example, at the same time as the notification in step S011. Alternatively, if the operator has performed the mounting procedure again, it is determined again whether the optical waveguide sensor chip 20 is mounted properly.

[How to Remove the Optical Waveguide Sensor Chip from the Measurement Unit]

Figure 12:
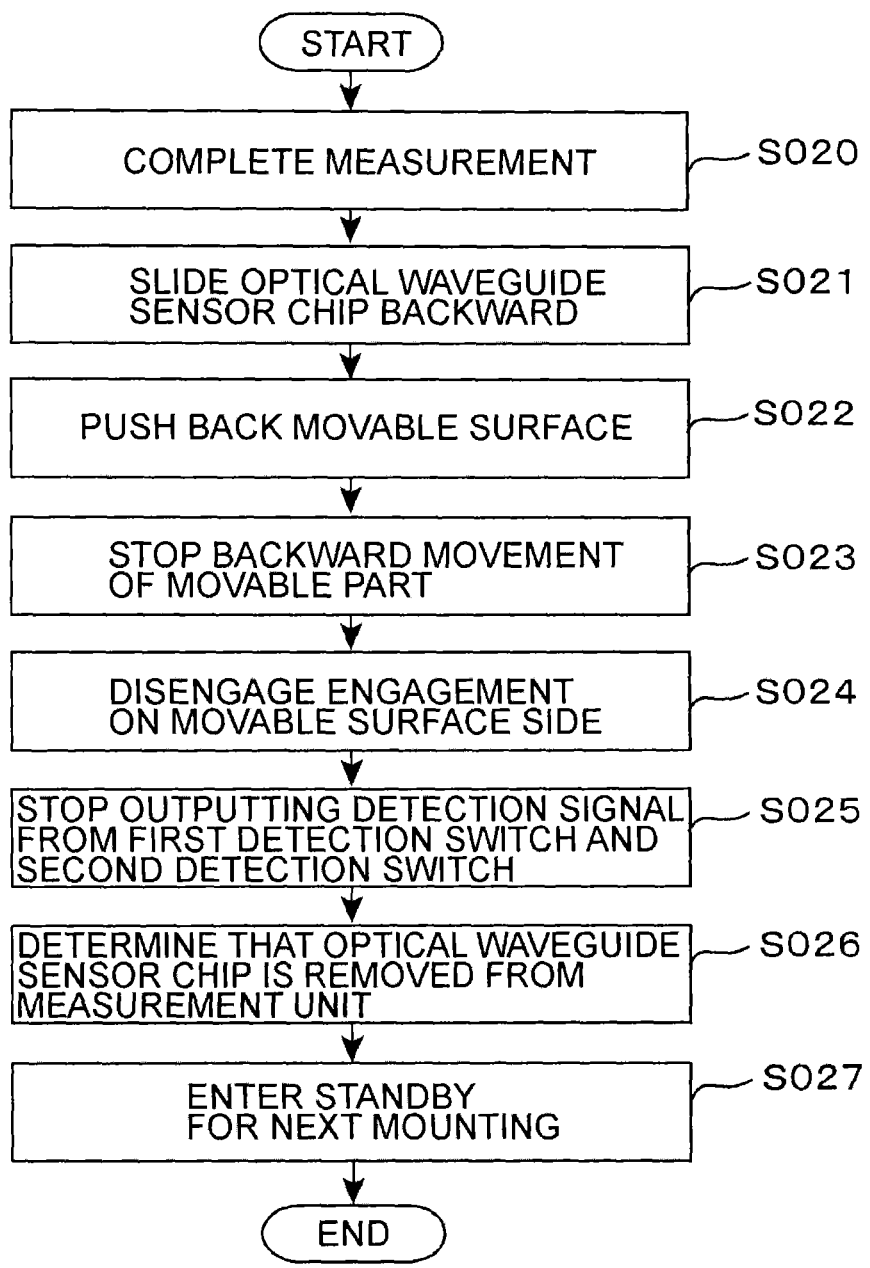
FIG. 12 is a flowchart of a procedure for removing the optical waveguide sensor chip from the measurement unit.

FIG. 12 is a flowchart of a procedure for removing the optical waveguide sensor chip 20 from the measurement unit 30.

Upon completion of the measurement in the optical waveguide measurement system 10 (step S020), the determination unit 85 receives information indicating the end of measurement. For example, when a measurement is performed after the application of an upward magnetic field to the optical waveguide sensor chip 20, the completion of the measurement is regarded as the end of measurement. Having been informed of the end of measurement from display on the display 81 or the like, the operator slides the optical waveguide sensor chip 20 backward on the measurement unit 30 (step S021). When the optical waveguide sensor chip 20 is slid backward, the movable surface 305a is pushed back (step S022). With this, the front-side engagement is disengaged.

After the backward movement of the movable part 305 is stopped by the stopper 307 (step S023), the operator disengages the engagement on the movable surface 305a side while moving the front portion of the optical waveguide sensor chip 20 upward (step S024). Thereby, the bottom surface 601 of the optical waveguide sensor chip 20 is separate from the holding surface 320, and thus the optical waveguide sensor chip 20 can be removed.

After the front portion of the optical waveguide sensor chip 20 is moved upward, the both the first detection switch 90a and the second detection switch 90b stop outputting a detection signal (step S025). Accordingly, it is determined that the optical waveguide sensor chip 20 is removed from the measurement unit 30 (step S026). In response to the determination result, the measurement unit 30 is placed in standby (initial state) for the next mounting until the start of the procedure of mounting the optical waveguide sensor chip 20 for the next measurement (step S027). In addition, in response to the determination result of step S026, for example, the system controller 70 controls the display 81 to display information indicating the removal of the optical waveguide sensor chip 20.

[How to Monitor the Mounting of the Optical Waveguide Sensor Chip]

Figure 13:
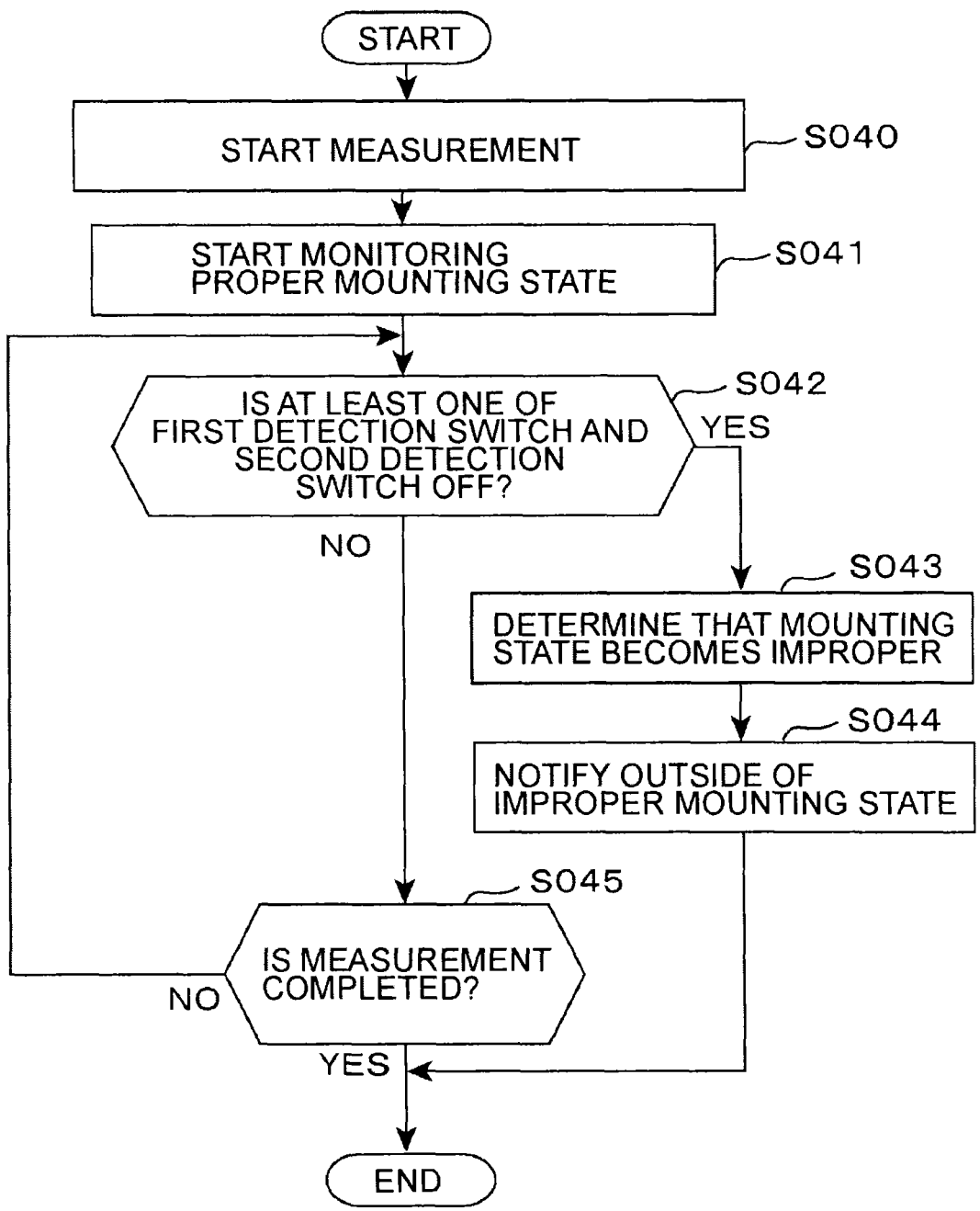
FIG. 13 is a flowchart of a procedure for monitoring the mounting of the optical waveguide sensor chip.

FIG. 13 is a flowchart of a procedure for monitoring the mounting of the optical waveguide sensor chip 20 on the measurement unit 30. When the optical waveguide sensor chip 20 is mounted on the measurement unit 30 properly and the optical waveguide measurement system 10 starts the measurement (step S040), the determination unit 85 starts monitoring the change of the mounting state of the optical waveguide sensor chip 20 (step S041). At the start of the monitoring, the determination unit 85 receives a detection signal from both the first detection switch 90a and the second detection switch 90b.

After the start of the monitoring, for example, there may be a case where the optical waveguide sensor chip 20 shifts due to an external force such as vibration and shock, and no signal is received from at least one of the first detection switch 90a and the second detection switch 90b (Yes in step S042). In such a case, the determination unit 85 determines that the mounting state of the optical waveguide sensor chip 20, which has been mounted properly, becomes improper (step S043).

The determination unit 85 feeds the system controller 70 with the determination result of the improper mounting state. In response to the determination result, the system controller 70 controls the output unit 80 to provide a notification of the improper mounting state to the outside (step S044). Alternatively, the system controller 70 may stop the measurement.

On the other hand, if it is determined in step S042 that a detection signal is received from both the first detection switch 90a and the second detection switch 90b (No in step S042), while the measurement continues (No in step S045), the determination unit 85 repeats the determination (monitoring) in step S042. In response to the end of measurement (Yes in step S045), the series of processes ends.

[First Modification]

In the above embodiment, the first detection switch 90a and the second detection switch 90b are located near the front contact surface 301a. Besides, the first detection switch 90a may be located near the right contact surface 302a, while the second detection switch 90b may be located near the left contact surface 303a. With this, it is possible to detect the inclination of the optical waveguide sensor chip 20 in the front-back and left-right directions of the measurement unit 30 with accuracy. However, the locations of the first detection switch 90a and the second detection switch 90b are not so limited. They may be located in any positions between the front contact surface 301a and a line that connects the light exit 51b and the light entrance 52b on the holding surface 320. That is, the locations of the first detection switch 90a and the second detection switch 90b can be determined by setting the height H at which each of them outputs a detection signal when pressed, for example, as follows.

The first detection switch 90a and the second detection switch 90b are arranged in an area between the light transceiver 50 and the front contact surface 301a in the front-back direction on the holding surface 320. The first detection switch 90a and the second detection switch 90b detect the inclination of the optical waveguide sensor chip 20 mounted on the measurement unit 30 in the front-back direction.

Figure 14:
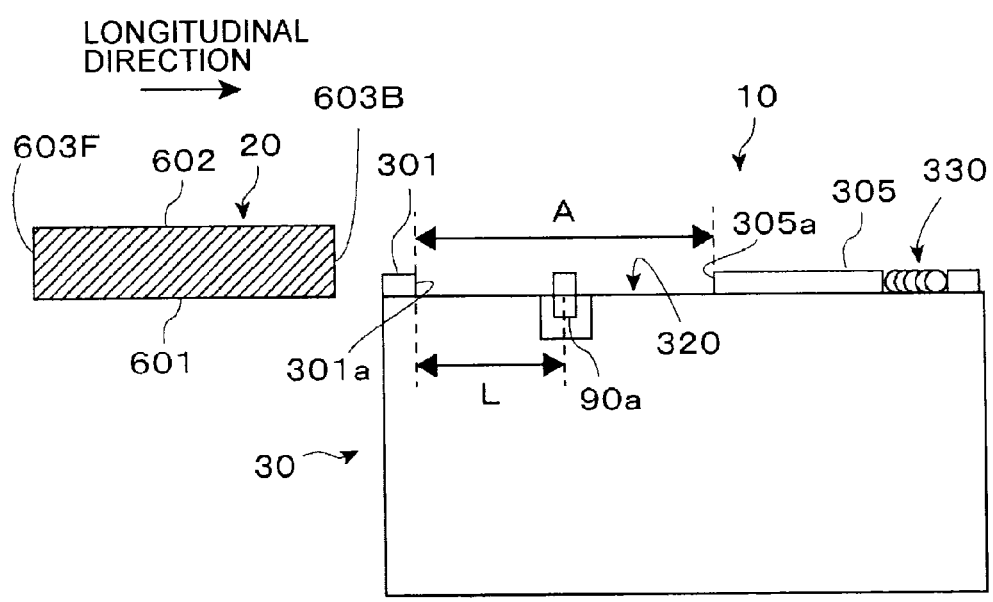
FIG. 14 is a schematic diagram illustrating an example of how to detect the inclination of the optical waveguide sensor chip in the front-back direction.
Figure 15:
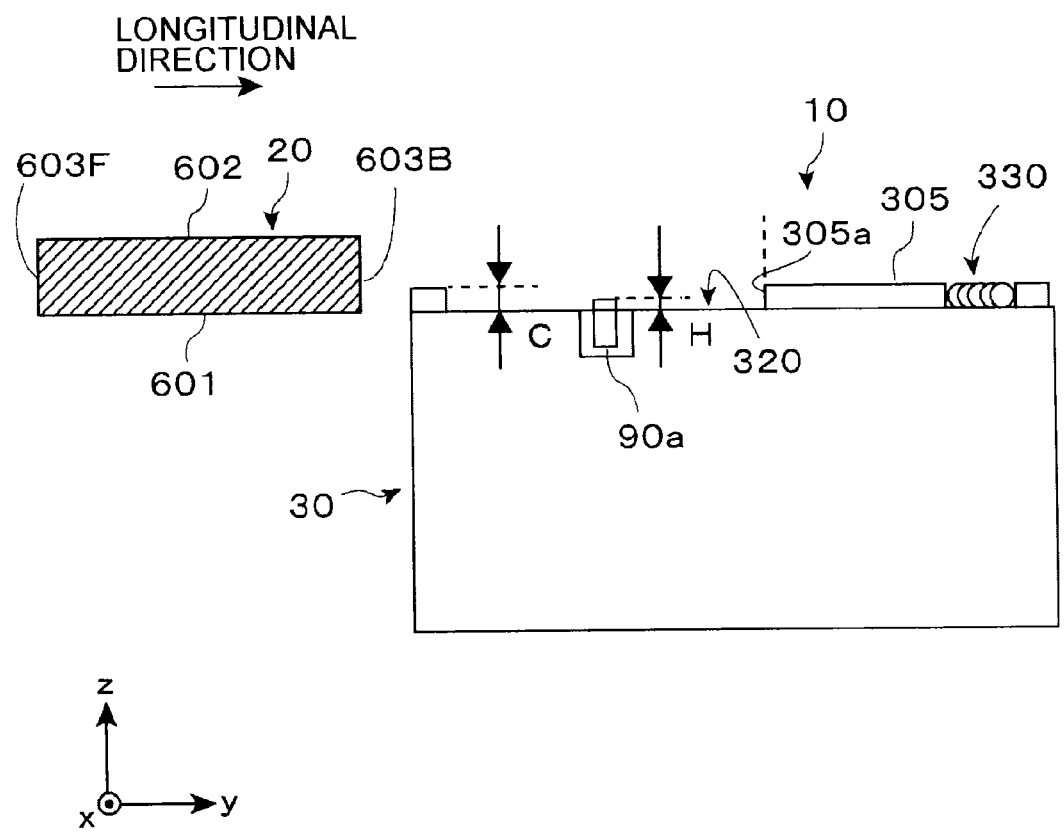
FIG. 15 is a schematic diagram illustrating an example of how to detect the inclination of the optical waveguide sensor chip in the front-back direction.
Figure 16:
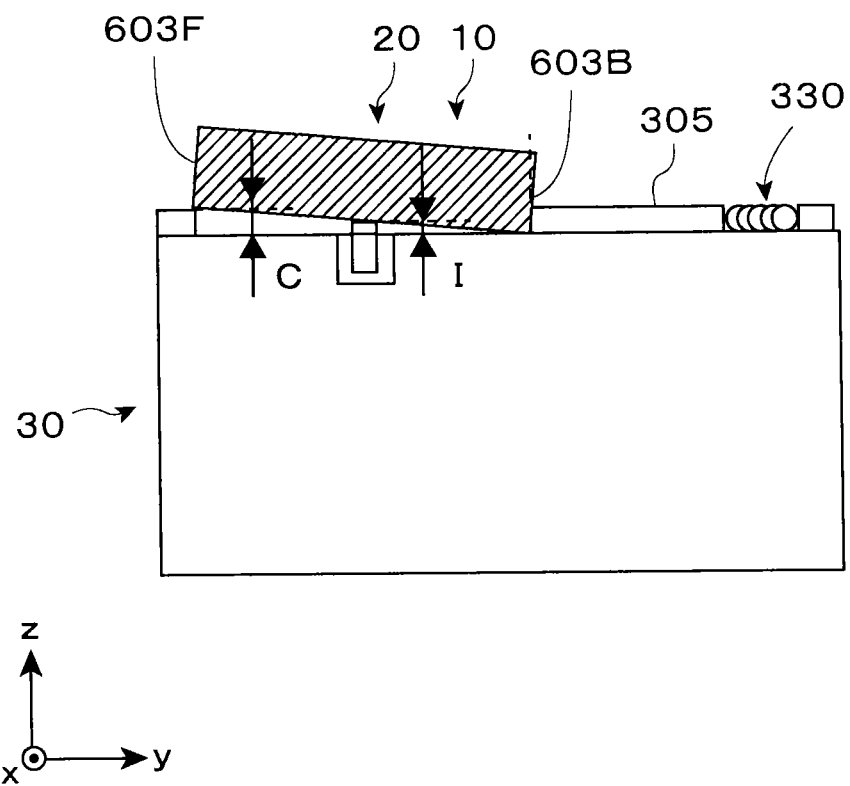
FIG. 16 is a schematic diagram illustrating an example of how to detect the inclination of the optical waveguide sensor chip in the front-back direction.

FIGS. 14 to 16 are schematic diagrams each illustrating an example of how to detect the inclination of the optical waveguide sensor chip 20 being mounted on the measurement unit 30 in the front-back direction. The figures illustrate the cross section of the measurement unit 30 taken along a line passing through the first detection switch 90a and parallel to the front-back direction. The figures also illustrate the cross section of the optical waveguide sensor chip 20 in a corresponding position. In the figures, the shaded area is intended to distinguishably indicate the optical waveguide sensor chip 20.

As illustrated in FIGS. 14 and 15, assuming first that C represents the height of the front contact surface 301a, A represents the distance in the front-back direction between the front contact surface 301a and the movable surface 305a, and L represents the distance in the front-back direction between the front contact surface 301a and the center axis of the first detection switch 90a. The first detection switch 90a and the second detection switch 90b are located in the same position in the front-back direction. It is also assumed that the first detection switch 90a is turned on when pressed down to height H. When pressed down and as high as the height H or lower, the first detection switch 90a is turned on, and when released from the pressing and becoming higher than the height H, it is turned off. The same applies to the height H of the second detection switch 90b.

FIG. 16 is a schematic diagram illustrating the optical waveguide sensor chip 20 mounted on the measurement unit 30 as running on the first contact part 301. Described below is how to detect the failure with the first detection switch 90a. When the optical waveguide sensor chip 20 is stranded on the first contact part 301, a gap of height I is created between the holding surface 320 and the bottom surface 601 of the optical waveguide sensor chip 20 in the position of the first detection switch 90a. At this time, the following relationship is formed: A:C=(A−L):I. Accordingly, the gap I between the holding surface 320 and the bottom surface 601 can be obtained as follows: I=C×(A−L)/A. Here, if the height of the gap I is higher than the height H at which the detection switch is turned off, it is detected that the optical waveguide sensor chip 20 is not mounted on the measurement unit 30 properly.

That is, since the following relationship is formed: I=C×(A−L)/A>H, the following relationship is obtained:

$$L < A(1-(H/C)) \tag{1}$$

The distance L in the front-back direction between the first detection switch 90a and the front contact surface 301a can be determined to satisfy the above equation (1). The location of the second detection switch 90b may be determined in the same manner as that of the first detection switch 90a.

Figure 17:
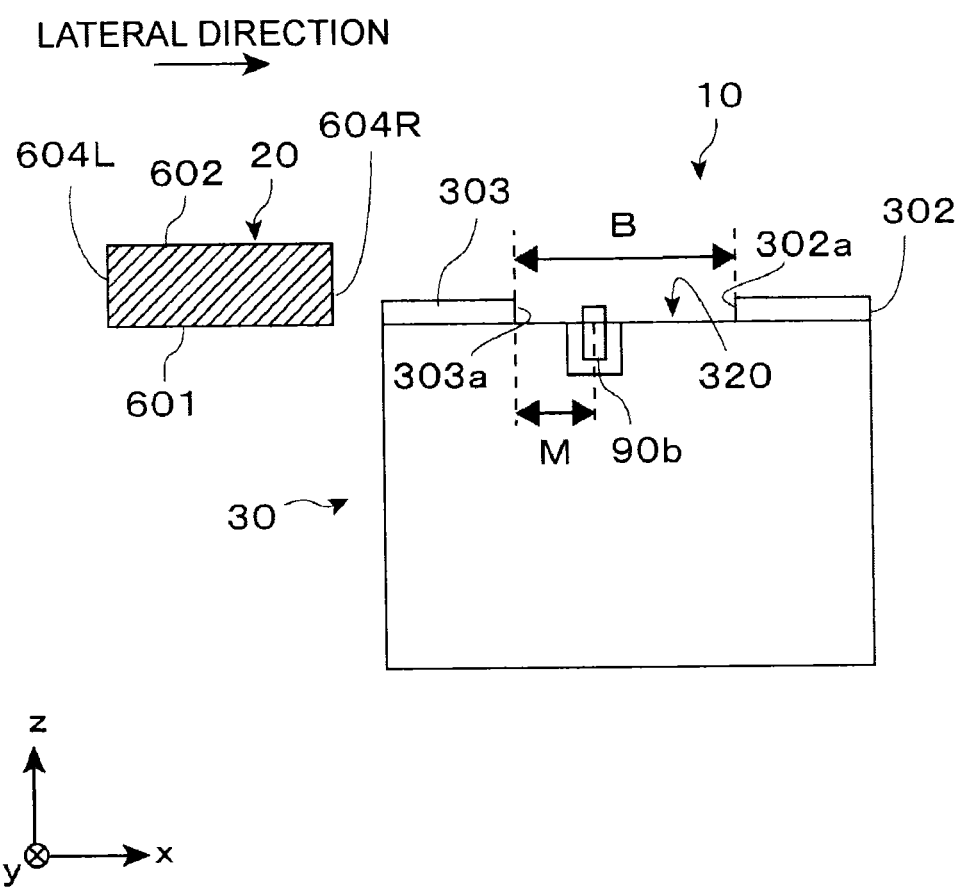
FIG. 17 is a schematic diagram illustrating an example of how to detect the inclination of the optical waveguide sensor chip in the left-right direction.
Figure 18:
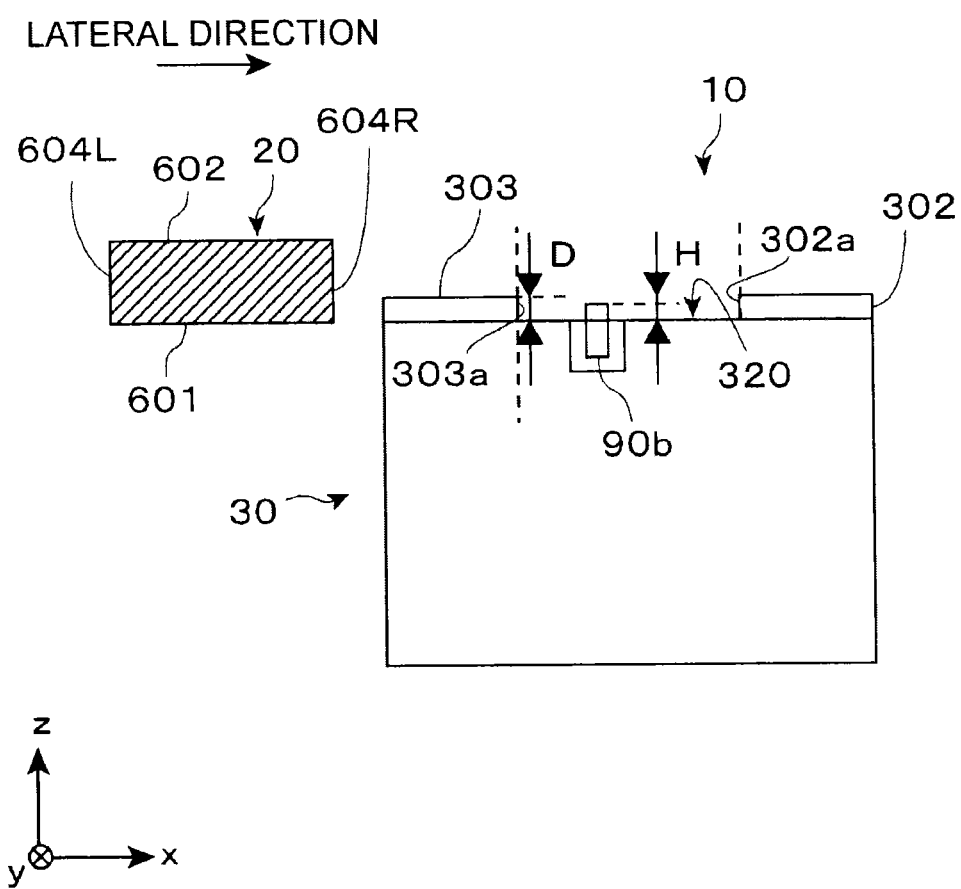
FIG. 18 is a schematic diagram illustrating an example of how to detect the inclination of the optical waveguide sensor chip in the left-right direction.
Figure 19:
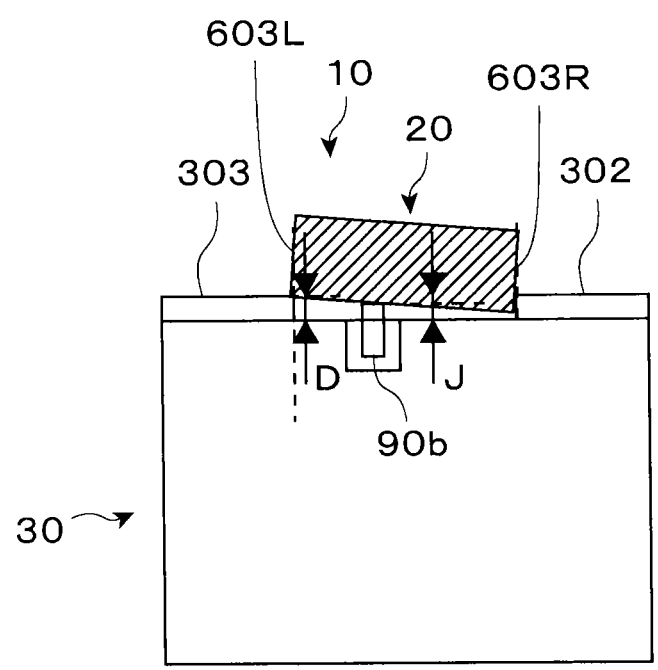
FIG. 19 is a schematic diagram illustrating an example of how to detect the inclination of the optical waveguide sensor chip in the left-right direction.

FIGS. 17 to 19 are schematic diagrams each illustrating an example of how to detect the inclination of the optical waveguide sensor chip 20 being mounted on the measurement unit 30 in the left-right direction. The figures illustrate the cross section of the measurement unit 30 taken along a line passing through the second detection switch 90b and parallel to the left-right direction. The figures also illustrate the cross section of the optical waveguide sensor chip 20 in a corresponding position. In the figures, the shaded area is intended to distinguishably indicate the optical waveguide sensor chip 20, and the first detection switch 90a is not illustrated.

As illustrated in FIGS. 17 and 18, assuming first that D represents the height of the left contact surface 303a, B represents the distance in the left-right direction between the third contact part 303 and the right contact surface 302a, and M represents the distance in the left-right direction between the third contact part 303 and the center axis of the second detection switch 90b. It is also assumed that, when pressed down and as high as the height H or lower, the second detection switch 90b is turned on, and when released from the pressing and becoming higher than the height H, it is turned off.

FIG. 19 is a schematic diagram illustrating the optical waveguide sensor chip 20 mounted on the measurement unit 30 as running on the third contact part 303. Described below is how to detect the failure with the second detection switch 90b. When the optical waveguide sensor chip 20 is stranded on the third contact part 303, a gap of height J is created between the holding surface 320 and the bottom surface 601 of the optical waveguide sensor chip 20 in the position of the second detection switch 90b. At this time, the following relationship is formed: B:D=(B−M):J. Accordingly, the gap J between the holding surface 320 and the bottom surface 601 can be obtained as follows: J=D×(B−M)/B. Here, if the height of the gap J is higher than the height H at which the detection switch is turned off, it is detected that the optical waveguide sensor chip 20 is not mounted on the measurement unit 30 properly.

That is, since the following relationship is formed: J=D×(B−M)/B>H, the following relationship is obtained:

$$M<(1-B(H/D)) \qquad (2)$$

The distance M in the left-right direction between the second detection switch 90b and the third contact part 303 can be determined to satisfy the above equation (2). By assuming that the optical waveguide sensor chip 20 runs on the second contact part 302, the location of the first detection switch 90a in the right-left direction may be determined in the same manner as that of the second detection switch 90b.

[Second Modification]

Figure 20:
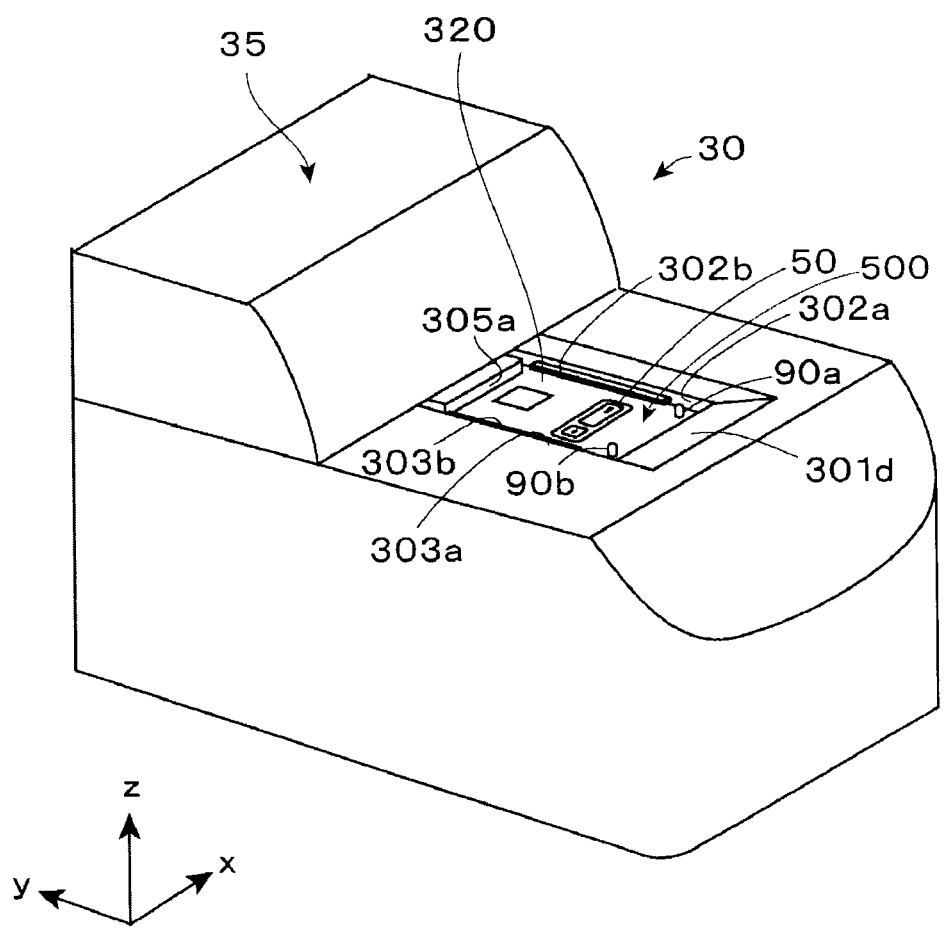
FIG. 20 is a perspective view of a measurement unit of an optical waveguide measurement system according to a modification of the embodiment.

FIG. 20 is a perspective view of the measurement unit 30 of the optical waveguide measurement system 10 according to another modification of the embodiment. As illustrated in FIG. 20, the measurement unit 30 is provided with a recess 500 on the upper surface 310. The recess forms the attachment part 300, i.e., the front contact surface 301a, the right contact surface 302a, and the left contact surface 303a. The movable surface 305a is located to face the front contact surface 301a. The bottom surface of the recess 500 forms the holding surface 320. The right contact surface 302a and the left contact surface 303a are provided with guide rails 302b and 303b, respectively. An inclined surface 301d is arranged in contact with the upper edge of the front contact surface 301a. The inclined surface 301d is inclined backward. The upper rear portion of the measurement unit 30 is the magnetic field unit 35 that applies a magnetic field to the optical waveguide sensor chip 20. As the magnetic field unit 35 slides forward, a device corresponding to the upper magnetic field applicator 21a moves above the optical waveguide sensor chip 20, and thereby an upward magnetic field can be applied to the reaction space 102.

The optical waveguide sensor chip 20 is inclined along the inclined surface 301d with respect to the holding surface 320 to be fitted in the attachment part 300. The optical waveguide sensor chip 20 is provided with flanges, the bottom surfaces of which are formed by the bottom surface 601. When the optical waveguide sensor chip 20 is inclined to be fitted in the attachment part 300, the flanges are inserted in the guide rails 302b and 303b to be guided backward. The height at which the guide rails 302b and 303b are arranged in their corresponding surfaces is larger than the thickness of the flanges. When the optical waveguide sensor chip 20 is moved backward, the back surface 603B of the optical waveguide sensor chip 20 abuts on the movable surface 305a. If the optical waveguide sensor chip 20 is further moved backward after it has abutted on the movable surface 305a, the movement of the movable part 305 is stopped by the stopper 307 (not illustrated). Thereafter, for example, the optical waveguide sensor chip 20 is mounted in the same manner as the procedure of steps S008 to S012 illustrated in FIG. 10.

Figure 21:
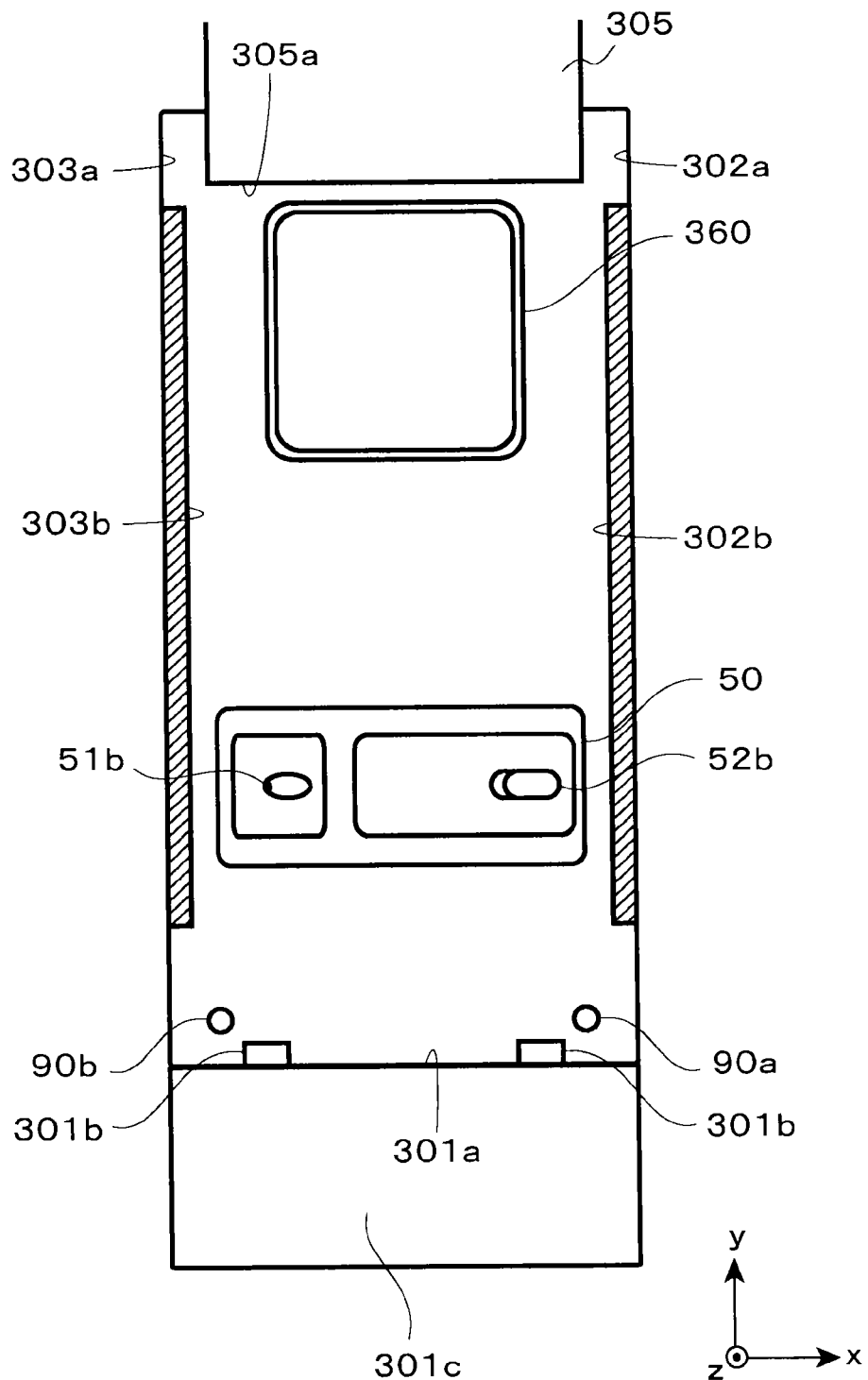
FIG. 21 is a top view of an example of an attachment part.
Figure 22:
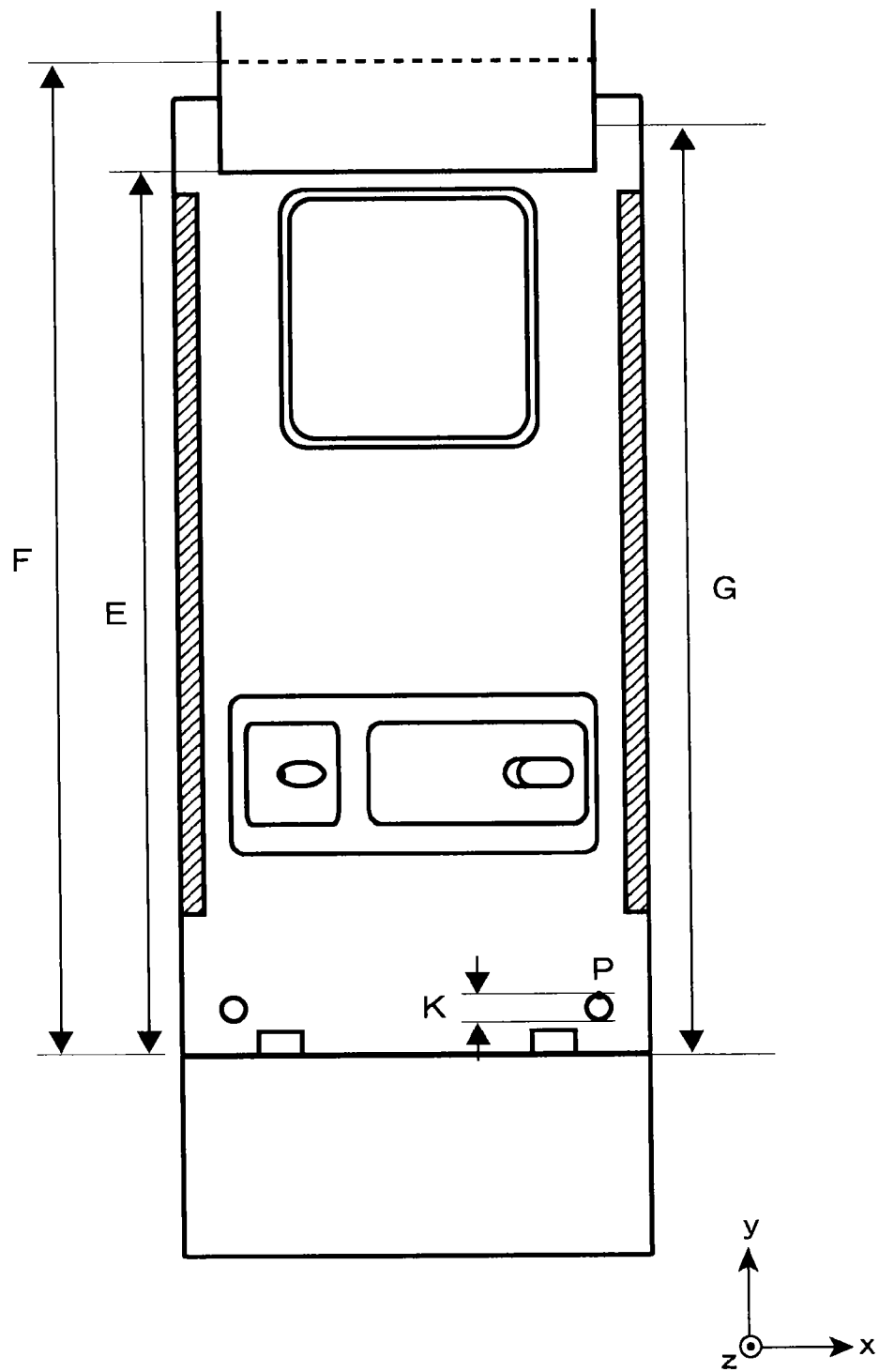
FIG. 22 is a top view of an example of the attachment part.

FIGS. 21 and 22 are top views of an example of the attachment part 300. The attachment part 300 includes, on the holding surface 320, a barcode reader 360, the light transceiver 50, the first detection switch 90a, and the second detection switch 90b. The barcode reader 360 reads a barcode on the optical waveguide sensor chip 20 and thereby identifies it. The light transceiver 50 includes the light exit 51b and the light entrance 52b. The light exit 51b and the light entrance 52b are arranged in parallel in the front-back direction on the holding surface 320. For example, laser light is emitted from the light exit 51b. Light emitted from the optical waveguide sensor chip 20 mounted on the measurement unit 30 enters through the light entrance 52b. The front contact surface 301a is provided with a plurality of the engagement claws 301C.

As described above, the right contact surface 302a and the left contact surface 303a are provided with the guide rails 302b and 303b extending from front to back, respectively. The guide rails 302b and 303b extend, for example, from positions behind the first detection switch 90a and the second detection switch 90b, and further extend backward. The guide rails 302b and 303b may be arranged to extend from positions behind the light transceiver 50, and further extend backward. The optical waveguide sensor chip 20 may run on the guide rails as being mounted on the attachment part 300. This can be detected in the same manner as when the optical waveguide sensor chip 20 runs on the second contact part 302 and the third contact part 303.

The first detection switch 90a and the second detection switch 90b may be arranged in positions that are exposed from the rear portion of the optical waveguide sensor chip 20 when the stopper 307 stops the backward movement of the movable part 305 pushed by the optical waveguide sensor chip 20. At this time, the first detection switch 90a and the second detection switch 90b are pressed down by the bottom surface 601 of the optical waveguide sensor chip 20.

In this case, the locations of the first detection switch 90a and the second detection switch 90b in the front-back direction may be determined as follows, for example. In FIG. 22, G indicates the longitudinal length of the optical waveguide sensor chip 20, E indicates the distance in the front-back direction between the front contact surface 301a and the movable surface 305a that is not pushed back, F indicates the distance in the front-back direction between the front contact surface 301a and the movable surface 305a that is pushed back and the movement is stopped by the stopper 307, and K indicates the width of the first detection switch 90a in the front-back direction.

The first detection switch 90a and the second detection switch 90b are identical. In addition, the first detection switch 90a and the second detection switch 90b are located in the same position in the front-back direction. Therefore, only one of them, i.e., the first detection switch 90a is taken to explain how to determine the location.

The distance E is shorter than the length G. Accordingly, when the optical waveguide sensor chip 20 is mounted on the attachment part 300, the movable surface 305a is pushed back by distance G−E. Then, a forward force is applied to the front surface 603F of the optical waveguide sensor chip 20 from the movable surface 305a by a biasing mechanism.

Thus, the optical waveguide sensor chip 20 is securely held by the first mechanism 340 in the longitudinal direction thereof.

When the movable surface 305a is pushed back by the front surface 603F of the optical waveguide sensor chip 20 and the movement of the movable part 305 is stopped by the stopper 307, the back surface 603B is located at a distance F–G from the front contact surface 301a toward the back. Accordingly, the first detection switch 90a is required to be in an area from the front contact surface 301a to the distance F–G toward the back on the holding surface 320. As the first detection switch 90a needs to be being pressed by the bottom surface 601 of the optical waveguide sensor chip 20, it is required to be arranged such that the position P of its rear end is located behind the position of the distance F–G. Therefore, the first detection switch 90a may be arranged such that the position P is located in a range between a position at the distance F–G from the front contact surface 301a toward the back and a portion at a distance F–G+K from the front contact surface 301a toward the back.

Figure 23:
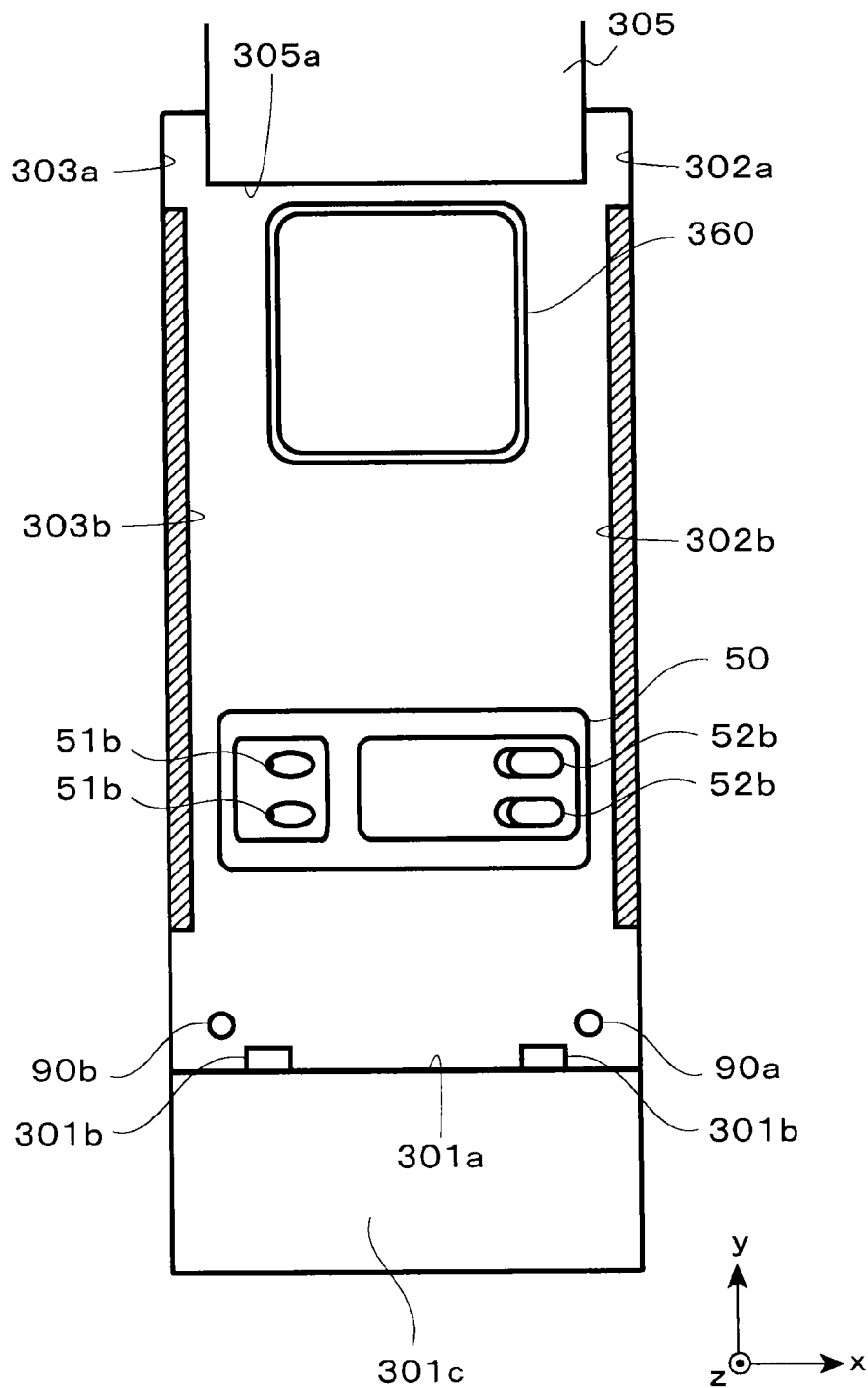
FIG. 23 is a top view of an attachment part of an optical waveguide measurement system according to another modification of the embodiment.

FIG. 23 is a top view of the attachment part 300 of the optical waveguide measurement system 10 according to still another modification of the embodiment. In this embodiment, the light transceiver 50 has two independent light transmitting/receiving functions. That is, a plurality of light beams (light flux) can be emitted through the light exit 51b. The light generator 51 includes, for example, two independent light sources (51a). On the other hand, the light receiver 52 can receive a plurality of light beams (light flux) emitted from the optical waveguide sensor chip 20 through the light entrance 52b. The light receiver 52 includes, for example, two independent light receiving devices (52a). There may be two light transceivers (50), each including the light exit 51b and the light entrance 52b arranged in parallel in the left-right direction, arranged in the front-back direction. In this case, the optical waveguide sensor chip 20 includes two independent sensing surfaces (101) in the lateral direction of the window 610, and a light beam is incident on each of the sensing surfaces 101. For example, in the optical waveguide sensor chip 20, by providing different functional layers (105) to the two independent sensing surfaces 101, two items can be measured by one test liquid. For example, as the examination of diabetes requires the measurement of hemoglobin as well as the measurement of A1C, these measurements can be performed with one optical waveguide sensor chip (20).

In this case, the optical waveguide sensor chip 20 is provided with the two independent sensing surfaces 101 in the lateral direction of the window 610. Accordingly, the lateral width of the optical waveguide part 3 that forms one sensing surface is reduced to half. Besides, light incident on the optical waveguide part 3 is laser light of a predetermined width. Therefore, if the optical waveguide sensor chip 20 is mounted on a position displaced in the front-back direction, the laser light cannot enter the optical waveguide part 3 properly, and thus may not be wave-guided therethrough properly. For example, there may be a case where light incident on the optical waveguide part 3 is diffusely reflected on the side surface of the optical waveguide part 3 and is attenuated in a place other than the sensing area 103, and also the diffusely reflected light becomes stray light. Since the stray light is irrelevant to measurement, it adversely affects the measurement result. For this reason, the optical waveguide sensor chip 20 has to be mounted on the measurement unit 30 properly also in the front-back direction. In the optical waveguide measurement system 10 of this embodiment, the optical waveguide sensor chip 20 can be securely held by the first mechanism 340 in the longitudinal direction thereof. Thus, the optical waveguide sensor chip 20 can be mounted properly also in the front-back direction.

Figure 24:
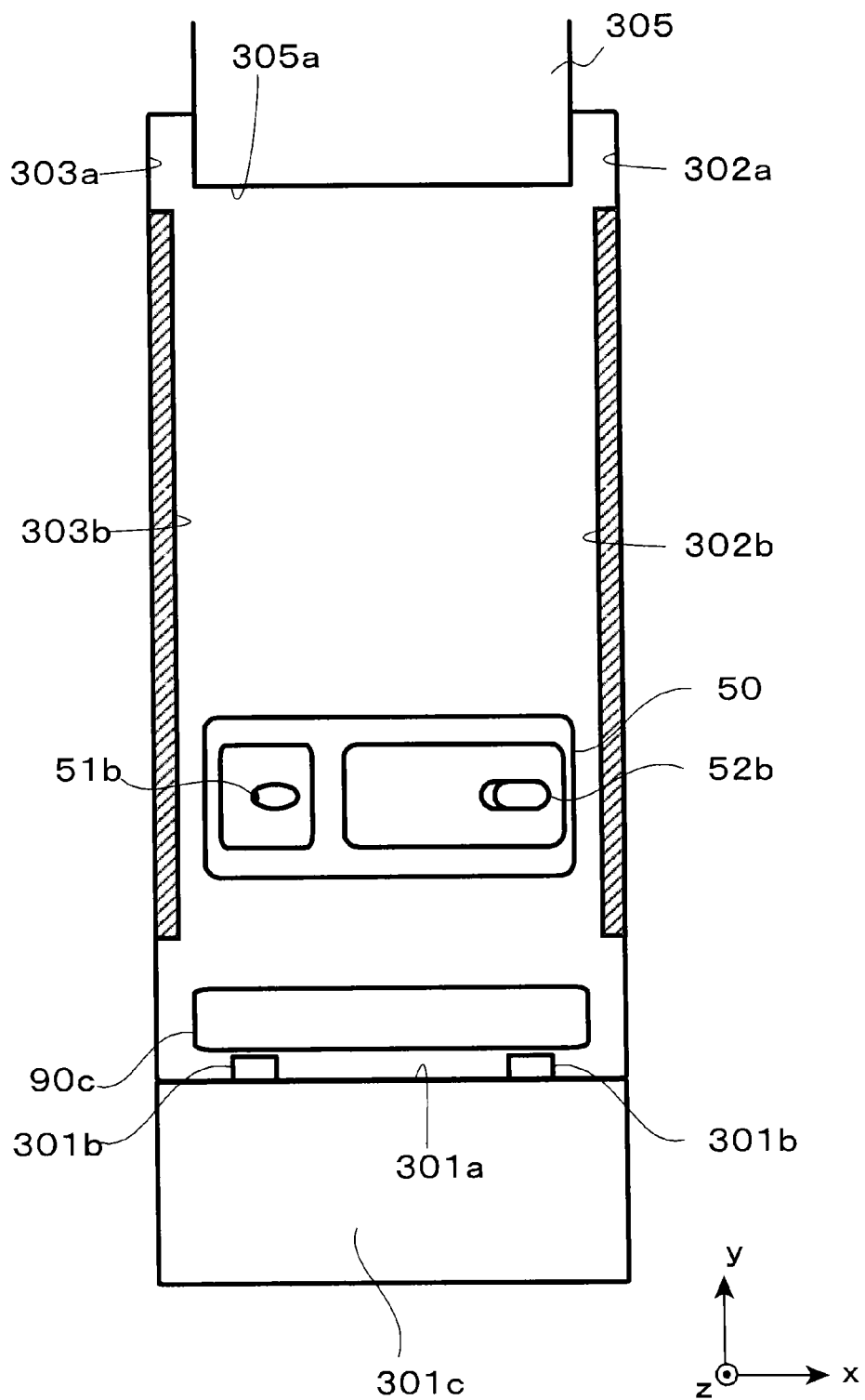
FIG. 24 is a top view of the attachment part in an example in which one contact sensor is used.

While an example is described above in which the first detection switch 90a and the second detection switch 90b as a plurality of contact sensors detect the contact state at two or more detection positions, a plurality of contact sensors are not necessarily required. FIG. 24 is a top view of the attachment part 300 in an example in which one contact sensor is used. An electrostatic panel 90c may be cited as an example of the one contact sensor that detects the contact state at two or more detection positions. The contact state is detected at two or more detection positions on the surface of the electrostatic panel 90c. Note that a pressure sensor may replace the electrostatic panel 90c.

While, in the embodiment, the optical waveguide measurement system 10 is configured such that the "first direction" corresponds to the y direction, and the "second direction" corresponds to the x direction, the configuration is not so limited. For example, the same configuration of the optical waveguide measurement system 10 as described above can be achieved if the "first direction" corresponds to the x direction, and the "second direction" corresponds to the y direction.

Figure 25:
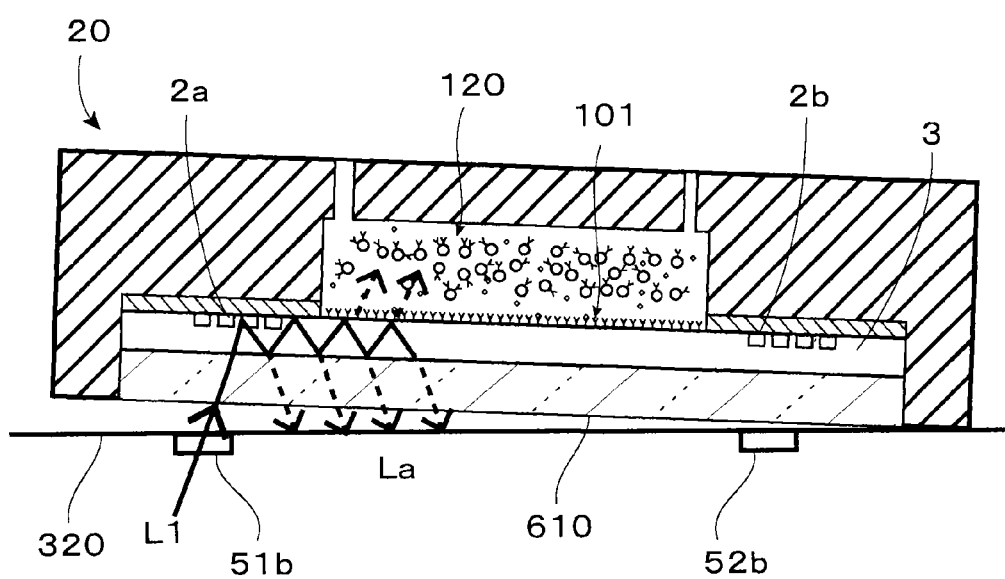
FIG. 25 is a cross-sectional view of the optical waveguide sensor chip mounted improperly.
Figure 26:
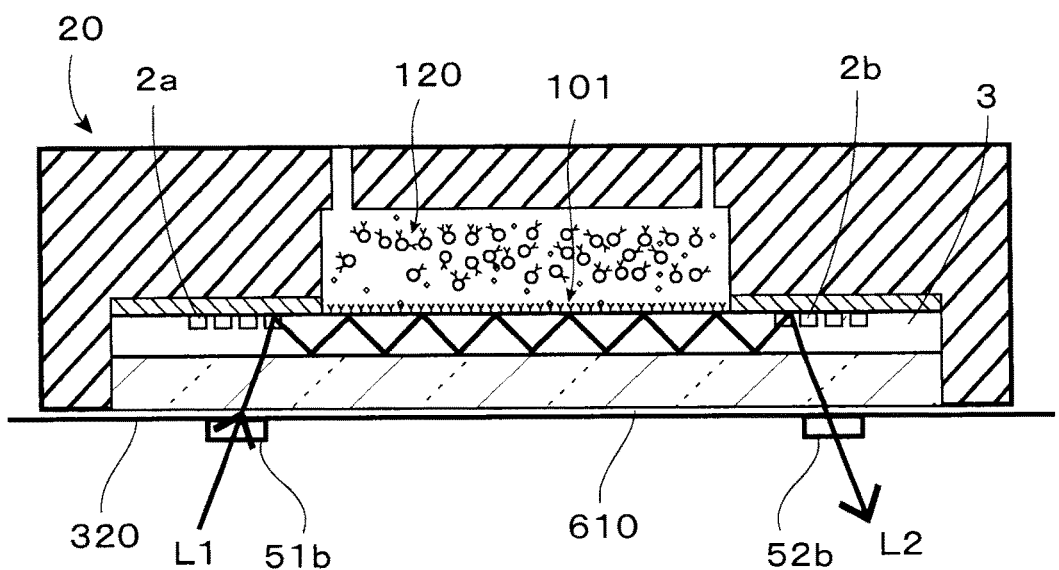
FIG. 26 is a cross-sectional view of the optical waveguide sensor chip mounted properly.

In the following, the optical waveguide sensor chip 20 mounted properly on the measurement unit 30 is described in comparison with that mounted improperly with reference to FIGS. 25 and 26. FIG. 25 is a cross-sectional view of the optical waveguide sensor chip 20 mounted improperly. That is, FIG. 25 is a cross-sectional view of the optical waveguide sensor chip 20 mounted with the bottom surface 601 at a predetermined angle with respect to the holding surface 320 of the measurement unit 30. FIG. 26 is a cross-sectional view of the optical waveguide sensor chip 20 mounted properly.

In FIGS. 25 and 26, the optical path indicated by a solid line is the one when the optical waveguide sensor chip 20 is mounted properly on the measurement unit 30, and L1 denotes incident light, while L2 denotes output light. In FIG. 25, broken lines indicate the optical path of output light La when the optical waveguide sensor chip 20 is mounted improperly.

<Example of Improper Mounting>

As illustrated in FIG. 25, the optical waveguide sensor chip 20 is mounted with the bottom surface 601 at an angle with respect to the holding surface 320. In other words, at least part of the bottom surface 601 of the optical waveguide sensor chip 20 floats a little from the holding surface 320. In this case, light emitted through the light exit 51b (not illustrated) is incident on the window 610 at an incident angle larger than the proper optical path of light (see FIG. 26) incident on the grating 2a when the optical waveguide sensor chip 20 is properly mounted. The light incident on the window 610 is refracted, and thereby incident on the optical waveguide part 3 at a still larger angle. The light incident on the optical waveguide part 3 is, for example, incident on the grating 2a at the entrance and is diffracted. At this time, the incident angle of the light incident on the grating 2a is large as compared to that of the proper optical path. Accordingly, the diffracted light cannot be wave-guided properly through the optical waveguide part 3, and is emitted therefrom to the outside (e.g., output light La). The output light La is emitted to the outside through the reaction space 102 and the window 610, and is not incident on the light entrance 52b properly. Therefore, the optical waveguide sensor chip 20 is required to be mounted on the measurement unit 30 such that the bottom surface 601 is parallel to the holding surface 320.

<<Displacement in the Left-right Direction>>

Since incident light is diffracted by the grating 2a a determined number of times under the condition that the optical waveguide sensor chip 20 is properly mounted, if the optical waveguide sensor chip 20 is mounted in a position displaced in the left-right direction, the light cannot be wave-guided properly through the optical waveguide part 3. For example, the incident light may not hit the grating 2a, or it may be diffracted by the grating 2a at the entrance a number of times other than the determined number, which may result in improper waveguiding. In the former case, the incident light is not totally reflected on the interface of the optical waveguide part 3 and output to the outside. In the latter case, the incident light diffracted by the grating 2a a number of times other than the determined number cannot generate a predetermined amount of near-field light in the sensing surface 101.

Even if the incident light is diffracted by the grating 2a at the entrance a determined number of times, the incident position and incident angle are shifted from proper ones in the grating 2a, resulting in an improper number of total reflection on the sensing corresponding surface. If the number is improper, as described above, the number of total reflections on the sensing corresponding surface falls out of the range set in advance. As a result, the measurement unit 30 cannot properly measure the density or the like of a test article in the reaction space 102. From these reasons, if the optical waveguide sensor chip 20 is mounted as being displaced in the left-right direction, precise measurement cannot be made in the optical waveguide measurement system 10. Therefore, the optical waveguide sensor chip 20 has to be mounted properly at least in the left-right direction.

<<Displacement in the Front-back Direction>>

Also when the optical waveguide sensor chip 20 is mounted on the measurement unit 30 improperly in the front-back direction, the incident light is irradiated to the side surfaces of the optical waveguide part 3, and is not properly wave-guided through the optical waveguide part 3. Accordingly, the optical waveguide sensor chip 20 has to be mounted properly also in the front-back direction. That is, light incident on the grating 2a at the entrance is required to enter the optical waveguide part 3 in a position and at an angle, which allow the light to be wave-guided properly.

In the optical waveguide measurement system 10 of the embodiment, the attachment part 300 includes the first mechanism 340 and the second mechanism 350 that hold the optical waveguide sensor chip 20 as surrounding it. Thus, the optical waveguide sensor chip 20 can be prevented from being displaced in the front-back direction as well as the left-right direction when mounted on the measurement unit 30. Moreover, since the first mechanism 340 has the movable surface 305a, the optical waveguide sensor chip 20 can be easily mounted on and removed from the measurement unit 30.

Further, the holding surface 320 is provided with the first detection switch 90a and the second detection switch 90b. These switches are located near the front contact surface 301a. With this, it is possible to detect the inclination of the optical waveguide sensor chip 20 in the front-back direction with accuracy when the optical waveguide sensor chip 20 is mounted on the measurement unit 30. Besides, the first detection switch 90a is located near the right contact surface 302a, while the second detection switch 90b is located near the left contact surface 303a on the holding surface 320. With this, it is possible to detect the inclination of the optical waveguide sensor chip 20 in the left-right direction with accuracy when the optical waveguide sensor chip 20 is mounted on the measurement unit 30. The measurement unit 30 determines that the optical waveguide sensor chip 20 is mounted improperly if at least one of the two detection switches does not output a detection signal when the optical waveguide sensor chip 20 is mounted on the attachment part 300. Thus, it is possible to detect the optical waveguide sensor chip 20 in a state where the bottom surface 601 is floating above the holding surface 320. Therefore, it is possible to reduce the work of the operator for checking proper mounting.

As described above, in the optical waveguide measurement system 10 of the embodiment, the measurement unit 30 is provided with the first detection switch 90a and the second detection switch 90b on the holding surface 320 in addition to the first mechanism 340 and the second mechanism 350. With this configuration, after mounted on the measurement unit 30, the optical waveguide sensor chip 20 is prevented from being displaced because being held in the front-back and left-right directions. The vertical displacement is prevented by detecting the floating of the optical waveguide sensor chip 20 and notifying the operator of improper mounting. Thus, the optical waveguide sensor chip 20 can be securely mounted on a predetermined position of the measurement unit 30.

In this manner, since the optical waveguide sensor chip 20 can be mounted on the measurement unit 30 properly, the incident light L1 is incident on the grating 2a in a proper position and at a proper angle. Therefore, the incident light L1 can be wave-guided properly through the optical waveguide part 3. Further, the incident light can be totally reflected on the sensing corresponding surface a proper number of times. Thus, a predetermined size of near-field light can be generated in the sensing surface 101. By sensing the density or the like of a test article in the reaction space 102 with the near-field light, the density or the like can be measured suitably.

Further, the distance between the movable surface 305a when the movable part 305 is pushed back and the rear ends of the first detection switch 90a and the second detection switch 90b is shorter than the longitudinal length of the optical waveguide sensor chip 20. This prevents the front surface 603F from being caught by the first detection switch 90a and the second detection switch 90b when the optical waveguide sensor chip 20 is being mounted on the attachment part 300. In addition, the distance between the movable surface 305a when the movable part 305 is pushed back and the front ends of the first detection switch 90a and the second detection switch 90b is longer than the longitudinal length of the optical waveguide sensor chip 20. Accordingly, when the optical waveguide sensor chip 20 is mounted on the attachment part 300, part of the upper surface of each of the first detection switch 90a and the second detection switch 90b is exposed from the vicinity of the front surface 603F of the optical waveguide sensor chip 20. This enables the operator to check the first detection switch 90a and the second detection switch 90b being pressed down from above the holding surface 320 to the detection position. This is at a stage prior to the state where the optical waveguide sensor chip 20 is ready to be mounted properly. Thus, the operator can check whether the optical waveguide sensor chip 20 can be mounted properly at the prior stage.

In the measurement unit 30, at least the holding surface 320 is made of dark colored material such as black material which easily absorbs light to reduce the effect on measurement due to external light, stray light, and the like. Further, in the optical waveguide measurement system 10 of the embodiment, the first detection switch 90a and the second detection switch 90b are made of bright colored material such as white material. Accordingly, the operator can easily figure out the position of the attachment part 300 by using the first detection switch 90a and the second detection switch 90b as targets when he/she places the optical waveguide sensor chip 20 on the attachment part 300. Further, the first detection switch 90a and the second detection switch 90b are located near the second contact part 302 and the third contact part 303, respectively. Thus, the operator can easily figure out that the locations of the first detection switch 90a and the second detection switch 90b correspond to the lateral ends of the optical waveguide sensor chip 20.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An optical measurement system configured to perform optical measurement of a subject and to have an optical waveguide sensor chip mounted thereon, the optical waveguide sensor chip having a space for accommodating the subject, the space being defined by a plurality of surfaces including a first surface on which a functional layer is formed and along which an optical waveguide part is provided, the optical measurement system comprising:
    a holding device configured to hold a bottom surface of the optical waveguide sensor chip, the holding device including a first window and a second window arranged along the optical waveguide part of the optical waveguide sensor chip so as to be spaced apart from the first window;
    a light transceiver configured to emit an incident light to be incident on the optical waveguide sensor chip through the first window, and receive output light that has passed through the first surface via the optical waveguide part from the second window;
    processing circuitry configured to process the output light to acquire information on the subject; and
    a plurality of contact sensors configured to detect whether all contact states are ON in two or more detection positions located along an array direction of the first window and the second window to provide detection results, wherein
    the processing circuitry is further configured to determine that the bottom surface of the optical waveguide sensor chip is in contact with the holding device based on the detection results from the contact sensors,
    the contact sensors are detection switches configured to be pressed down by the bottom surface of the optical waveguide sensor chip,
    for each contact sensor of the plurality of contact sensors, a position of the contact sensor satisfies $L<A(1-(H/C))$, A being a distance between a fixed holder and a movable holder, L being a distance between the fixed holder and the contact sensor, C being a height of the fixed holder, and H being a height of the contact sensor when the contact sensor is pressed down to be in the ON state, and
    for one of the plurality of contact sensors, the position of the contact sensor further satisfies $M<(1-B(H/D))$, M being a distance in the left-right direction between a center axis of the contact sensor and a left contact part, B being a distance in the left-right direction between a right contact part and the left contact part, and D being a height of the left contact part,
    wherein the holding device includes:
    the fixed holder;
    the movable holder configured to hold the optical waveguide sensor chip against the fixed holder from two of four side surfaces of the optical waveguide sensor chip; and
    a mechanism configured to bias the movable holder toward the fixed holder.

2. The optical measurement system of claim 1, wherein the plurality of contact sensors are located closer to the fixed holder than the first window and the second window are.

3. The optical measurement system of claim 1, wherein the mechanism includes a movement limiter configured to limit vertically upward movement of the optical waveguide sensor chip, the movement limiter being an engagement claw.

4. The optical measurement system of claim 3, further comprising a side surface holder including a pair of contact surfaces configured to be in contact with two other side surfaces of the four side surfaces of the optical waveguide sensor chip, the other two of four side surfaces extending perpendicular to the two of four side surfaces, the contact surfaces being located in positions perpendicular to the fixed holder and the movable holder and facing each other, wherein
    each of the contact sensors is located near one of the contact surfaces.

5. The optical measurement system of claim 1, wherein the plurality of contact sensors are located near the fixed holder.

6. The optical measurement system of claim 4, wherein the movement limiter is configured to be capable of engaging with an engagement part on a side surface of the optical waveguide sensor chip, and includes guide rails each extending on one of the side surface holders toward the movable holder from a position that is closer to the movable holder than the contact sensor is.

7. The optical measurement system of claim 1, further comprising
    the optical waveguide sensor chip that resides within the holding device, wherein
    the optical waveguide sensor chip includes
        a first grating on the first window side, configured to deflect the light to be incident on the optical waveguide part, and
        a second grating on the second window side, configured to deflect the light to be emitted from the optical waveguide part, and
        an array direction of the fixed holder and the movable holder is perpendicular to an array direction of the first grating and the second grating.

8. The optical measurement system of claim 1, further comprising the optical waveguide sensor chip that resides within the holding device, wherein
    the optical waveguide sensor chip includes
        a first grating on the first window side, configured to deflect the light to be incident on the optical waveguide part, and
        a second grating on the second window side, configured to deflect the light to be emitted from the optical waveguide part, and an array direction of the fixed holder and the movable holder is parallel to an array direction of the first grating and the second grating.

9. The optical measurement system of claim 1, wherein the holding surface has a color different from the plurality of contact sensors.

10. The optical measurement system of claim 1, wherein the light transceiver is configured to emit a plurality of light fluxes through the first window and receive a plurality of light fluxes that has passed through the first surface via the optical waveguide part from the second window, and the processor is configured to process each of the light fluxes received by the light transceiver to acquire a plurality of pieces of information.

* * * * *